(12) United States Patent
Subramanya et al.

(10) Patent No.: US 6,642,529 B1
(45) Date of Patent: Nov. 4, 2003

(54) METHODS FOR THE AUTOMATED TESTING OF RETICLE FEATURE GEOMETRIES

(75) Inventors: Sudhir G. Subramanya, Fremont, CA (US); Clifford Takemoto, San Jose, CA (US); Satyendra S. Sethi, Pleasanton, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/538,027

(22) Filed: Mar. 28, 2000

(51) Int. Cl.[7] .................. G01N 21/00; H01J 37/00; G09R 9/00
(52) U.S. Cl. .................. 250/492.2; 250/492.1; 250/492.22; 250/397; 250/398; 250/305; 250/306; 250/302; 250/308; 250/309; 250/310; 250/556; 382/145; 356/237.1; 356/237.2; 356/237.3; 356/237.4; 356/237.5; 356/376; 355/54; 355/78
(58) Field of Search .................. 250/492.1, 492.2, 250/492.22, 492.3, 492.21, 305, 306, 307, 308, 310, 311, 556; 382/145; 356/237.5, 237.1, 237.2, 376; 355/78, 54

(56) References Cited

U.S. PATENT DOCUMENTS

| | | | |
|---|---|---|---|
| 4,527,070 A | 7/1985 | Matsui et al. |
| 5,475,766 A | 12/1995 | Tsuchiya et al. |
| 5,767,974 A | 6/1998 | Higashiguchi et al. |
| 5,804,340 A | 9/1998 | Garza et al. |
| 5,850,467 A | 12/1998 | Matsui et al. |
| 6,014,456 A | 1/2000 | Tsudaka |
| 6,038,020 A | 3/2000 | Tsukuda |

*Primary Examiner*—John R. Lee
*Assistant Examiner*—David A. Vanore
(74) *Attorney, Agent, or Firm*—Peter Zawilski

(57) ABSTRACT

A method for inspecting features on a reticle is provided. The method includes providing a layout design of a test feature and transferring the layout design of the test feature onto the reticle. After the test feature is transferred onto the reticle, an image of the transferred layout design is captured to determine whether or not the transfer is acceptable. This determination is made by comparing the captured image of the transferred layout design against the layout design of the test feature. The comparison ascertains deviations between the captured image and the layout design and determines if the deviations fall within a user specified range.

31 Claims, 19 Drawing Sheets

Test Results

| | Pass/Fail |
|---|---|
| M1 | P |
| M2 | P |
| M3 | P |
| M4 | F |

METHODS FOR THE AUTOMATED TESTING OF RETICLE FEATURE GEOMETRIES

BACKGROUND OF THE INVENTION

1. Field of the Invention

The present invention relates to the manufacture of reticles used in fabricating semiconductor devices. More particularly, the present invention relates to determining the accuracy of the reticle formation and a method for determining distortions in the patterning of the reticle such that the method enables a user to decide whether or not the reticle should be used to form patterns on films deposited over semiconductor wafers.

2. Description of the Related Art

Today's semiconductor devices are continually being pushed to meet stricter demands. As devices using this technology inundate the marketplace, consumers place higher demands on the devices. These demands include smaller, more compact devices with greater functionality.

Semiconductor devices employ various circuitry in a chip to perform user specified functions. As is well known, the circuitry consists of various metallization lines, dielectric layers and other components interconnected throughout the entire chip. The metallization lines and dielectric layers are formed by first depositing a metal layer or a dielectric layer onto a semiconductor wafer. The metallization lines and dielectric layers are deposited on the semiconductor wafer by spin coating, chemical vapor deposition, deposition and other standard techniques of applying films onto wafers. After deposition, the film must be patterned to form a metallization layer or other component on the semiconductor wafer.

Now making reference to FIG. 1, a photoresist layer 104 is applied by spin coating photoresist over a deposited layer 101. Once the photoresist layer 104 is spin coated onto a wafer 102, the wafer 102 is patterned. The wafer 102 is placed into a stepper that contains a reticle 100 which has a proper pattern 100a for the deposited layer 101. The stepper machine transfers the image of the reticle 100 onto the semiconductor wafer 102 by passing a light source 103 through the reticle 100. The reticle 100 acts as a filter and only allows a certain pattern of light from the light source 103 to pass through and onto the photoresist layer 104 of the wafer 102. The pattern of the light passing through the reticle 100 is the pattern for a feature to be formed on the deposited layer 101 of the semiconductor wafer 102. The light 103 passing through the reticle 100 and onto the photoresist layer 104 will react with the photoresist layer 104. The reaction will affect the solubility of the exposed portions of the photoresist layer 104 when the photoresist layer 104 is immersed in a solvent. For example, if the photoresist is positive, it will become more soluble as it is exposed to the light. Therefore, photoresist 104a will become soluble when it is subjected to an immersion process (not shown), leaving the pattern defined by photoresist 104b. If the photoresist is negative, the photoresist will become more insoluble as it is exposed to the light. For example, the photoresist 104b will dissolve and the photoresist 104a will remain after the photoresist 104 subjected to an immersion process (not shown).

The pattern for the reticle which is used to pattern the film is first designed in an integrated computer design (IC) using a computer aided design program. After the design is made, the features of the design which are to be formed on the wafer must be transferred to the reticle. For example, what will define a metallization line in the digital IC design will be transferred to the reticle in order for it to be imaged onto the photoresist 104 of the semiconductor wafer. The reticle is a glass plate which will be placed into the stepper. Chromium is deposited on top of the glass plate by any standard technique. A photoresist layer is then spin coated over the chromium layer. Once the photoresist is deposited over the chromium layer, the photoresist is patterned with either a laser tool or using an electron beam direct write exposure technique. After the image is formed on the reticle, the reticle is ready to pattern films on semiconductor wafers.

However, in most cases, the image that appears on the reticle will not be the same image that is in the computer digital IC layout. For example, a rounding effect may occur at sharp edges, such as those edges used to define a square feature on the reticle. The square feature will have rounded edges approximating parabolas instead of edges approximating the corners of the square. This effect occurs due to well known proximity effects and because features of the digital IC design are being designed at such a small scale that it is difficult to reproduce the same digital image on the reticle.

In order to avoid these problems, designers typically employ serifs at the edges of a feature in the digital IC design which is transferred to the reticle. For example, serifs would be placed in the corners of the aforementioned square to compensate for the rounding effect which takes place in the corners of the square. The serif increases the amount of area in each of the corners to compensate for anticipated losses. Thus, the area created by the serifs will compensate for the loss of area due to the rounding of the edges within a square feature not containing the serifs.

Nonetheless, the use of serifs in the prior art creates problems because many changes may be required to get proper image formation on a wafer. With the current available methods, a user is unable to determine how all the changes (e.g., proximity effects) will change the original digital IC design after it is transposed onto a reticle and finally onto the film of a semiconductor wafer. Furthermore, the prior art checks on reticles only involved checking proximity effects due to close line separations, while no checks can be made to determine problems with the overall image, such as corners. As a consequence, the image formed on the reticle may not function as originally intended because the image has experienced too many distorting changes which are not appreciated until the reticle transfers the patterns to photoresist.

Typically, even before a reticle will be used to form patterns on the film, a determination must be made as to the quality of the reticle (e.g., how planar is the glass, imperfections on the surface of the reticle and concavities which render the reticle impractical for use). This determination is usually done by placing test patterns on the reticle and then ascertaining how closely the design on the reticle conforms to the design in the digital IC layout.

However, as mentioned above, the quality of the reticle can only be tested by placing the reticle with the test pattern into the stepper and forming patterns on a film of the wafer itself. This greatly slows down the process time since this requires a user to wait until the photoresist develops before one may determine the accuracy of the photoresist image. Also, a user is precluded from making a series of reticles without worrying about whether or not the reticles form the desired images on the films. Instead, after one reticle is made, a user must use-the developed photoresist layer to determine the reticle's accuracy. Furthermore, as is well known in the art, there is a general push to generate reticles more quickly in order to facilitate the manufacture of semiconductor wafers.

As a result, the current methods of checking reticles is time consuming and expensive. A user must actually place the reticle into the stepper and print the reticle image with photolithography before a determination can be made as to the quality of the reticle. Also, the time of using the stepper, developing the photoresist and using the wafer increase the cost of ascertaining the quality of a reticle.

In view of the foregoing, there is a need for a method of determining the accuracy of a particular reticle which avoids the problems of the prior art. This new method should facilitate checking reticles in a time efficient and cost efficient manner.

SUMMARY OF THE INVENTION

Broadly speaking, the present invention fills these needs by providing a method for inspecting features on a reticle. It should be appreciated that the present invention can be implemented in numerous ways, including as a process, an apparatus, a system, a device or a method. Several inventive embodiments of the present invention are described below.

In one embodiment, a method for inspecting features on a reticle is disclosed. A layout design of a test feature is first provided and then the layout design is transferred to a reticle. After the layout design is transferred to the reticle, an image of the transferred layout design is captured. The captured image of the transferred layout design is compared against the layout design of the test feature to ascertain deviations between the captured image and the layout design once the image is captured.

In another embodiment, a method of ascertaining a degree of distortion of features on a reticle is disclosed. A test feature is provided and then transferred to a reticle to create a transferred test feature. After the test feature is transferred, the transferred test feature is compared to the test feature to ascertain the degree of distortion. The transferred test feature is also compared with the test feature to determine whether modifications of the test feature are necessary to compensate for the degree of distortion of the transferred test feature.

In yet another embodiment, a computer readable media having program instructions for carrying out a method of ascertaining a degree of distortion of features of a reticle is disclosed. Programming instructions provide test features and transfer the test feature to a reticle to create a transferred test feature. Programming instructions also compare the transferred test feature to the test feature to ascertain the degree of distortion and whether modifications of the test feature are necessary to compensate for the degree of distortion of the transferred test feature.

The many advantages of the present invention should be recognized. The present invention gives a user a simple way of determining the acceptability of a reticle by measuring features transferred onto a reticle against the digital version of the features. This method avoids the prior art problems of having to develop photoresist on a semiconductor wafer in order to ascertain the accuracy of a reticle. As such, this method greatly reduces costs and time in determining the acceptability of reticles.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings. Therefore, like reference numerals designate like structural elements.

FIG. 15 shows a pass or fail report in accordance with the embodiment of the present invention.

DETAILED DESCRIPTION OF THE PREFERRED EMBODIMENTS

A method of inspecting distortions to feature geometries formed on reticles is disclosed. In the following description, numerous specific details are set forth in order to provide a thorough understanding of the present invention. It will be understood, however, to one skilled in the art, that the present invention may be practiced without some or all of these specific details. In other instances, well known process operations have not been described in detail in order not to unnecessarily obscure the present invention.

Figure 1:
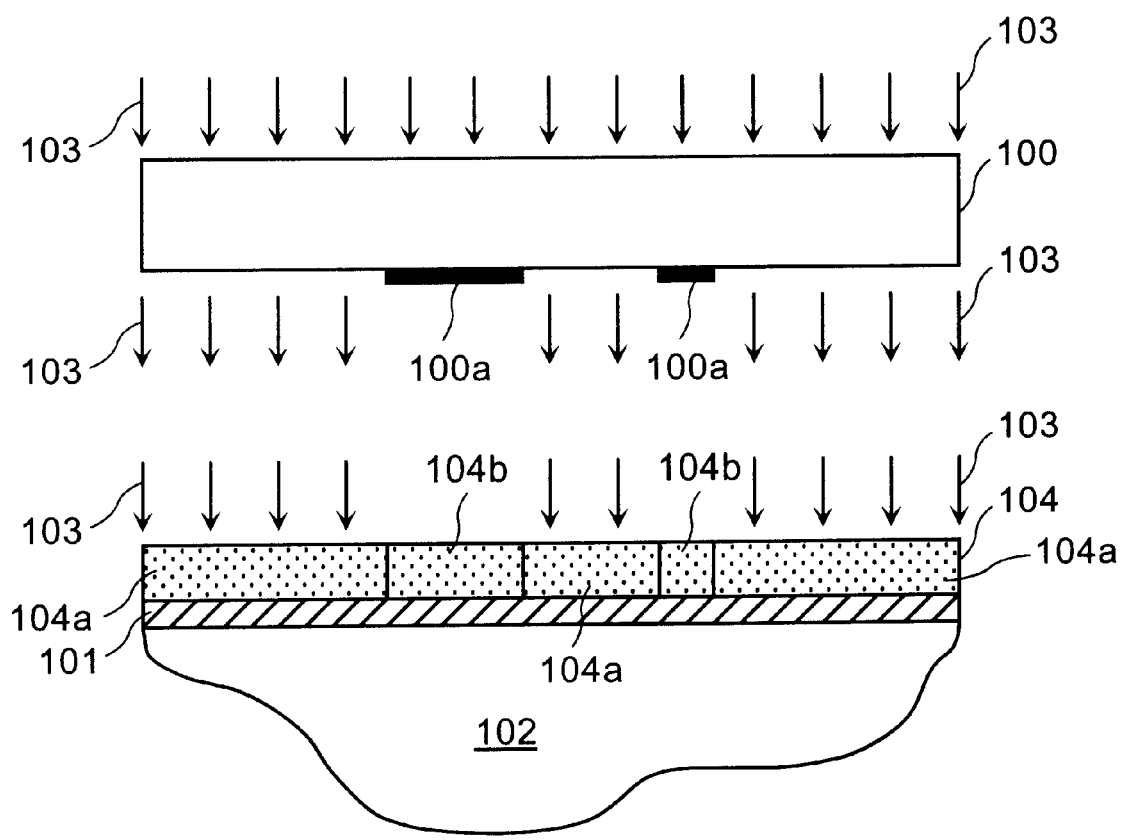
FIG. 1 shows a prior art method of determining the accuracy of a test feature on reticle by forming a pattern on a layer of photoresist deposited over a semiconductor wafer.
Figure 2A:
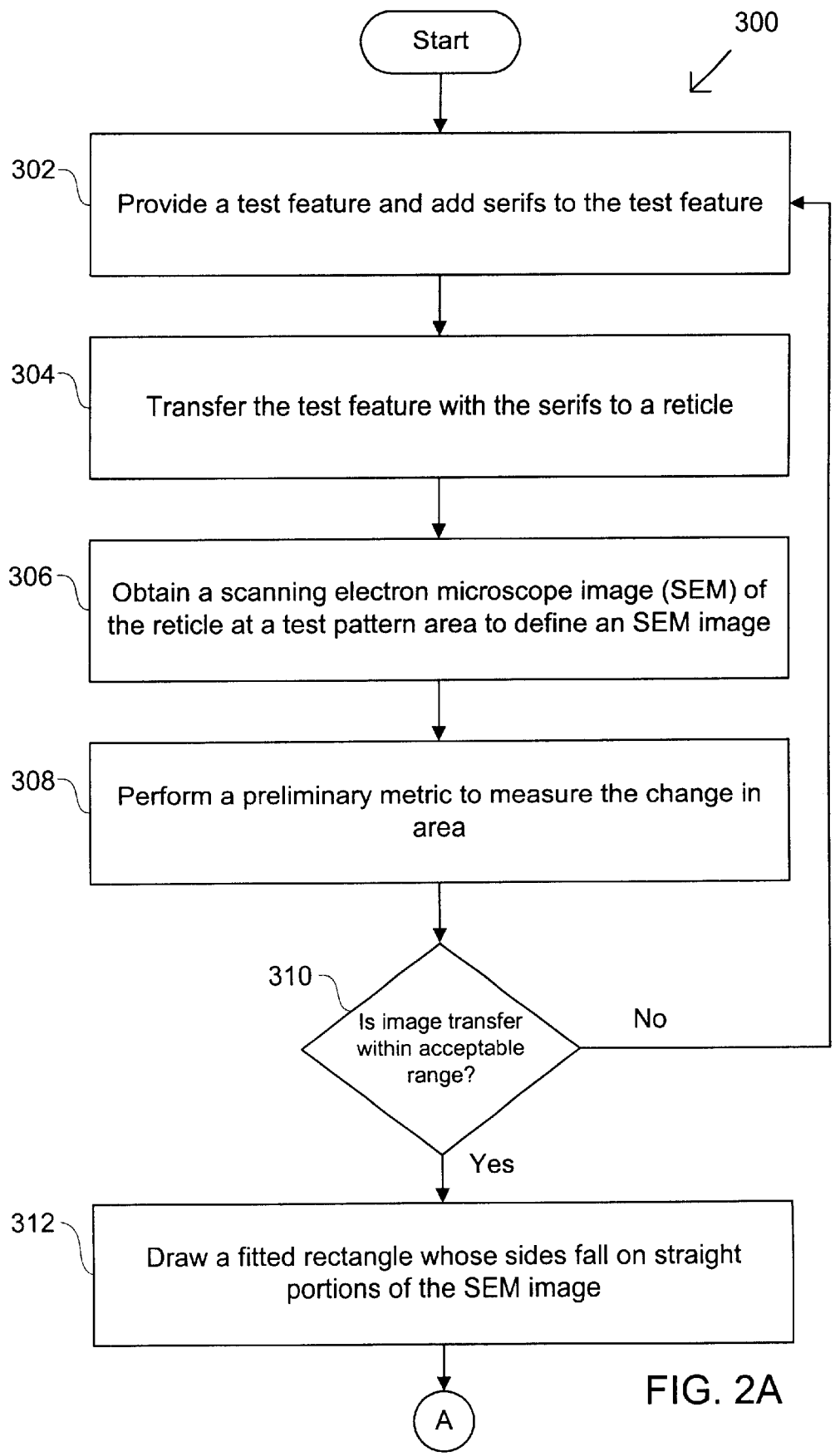
FIGS. 2A–2E are flowcharts showing an operation for inspecting features on a reticle in accordance with one embodiment of the present invention.
Figure 2B:
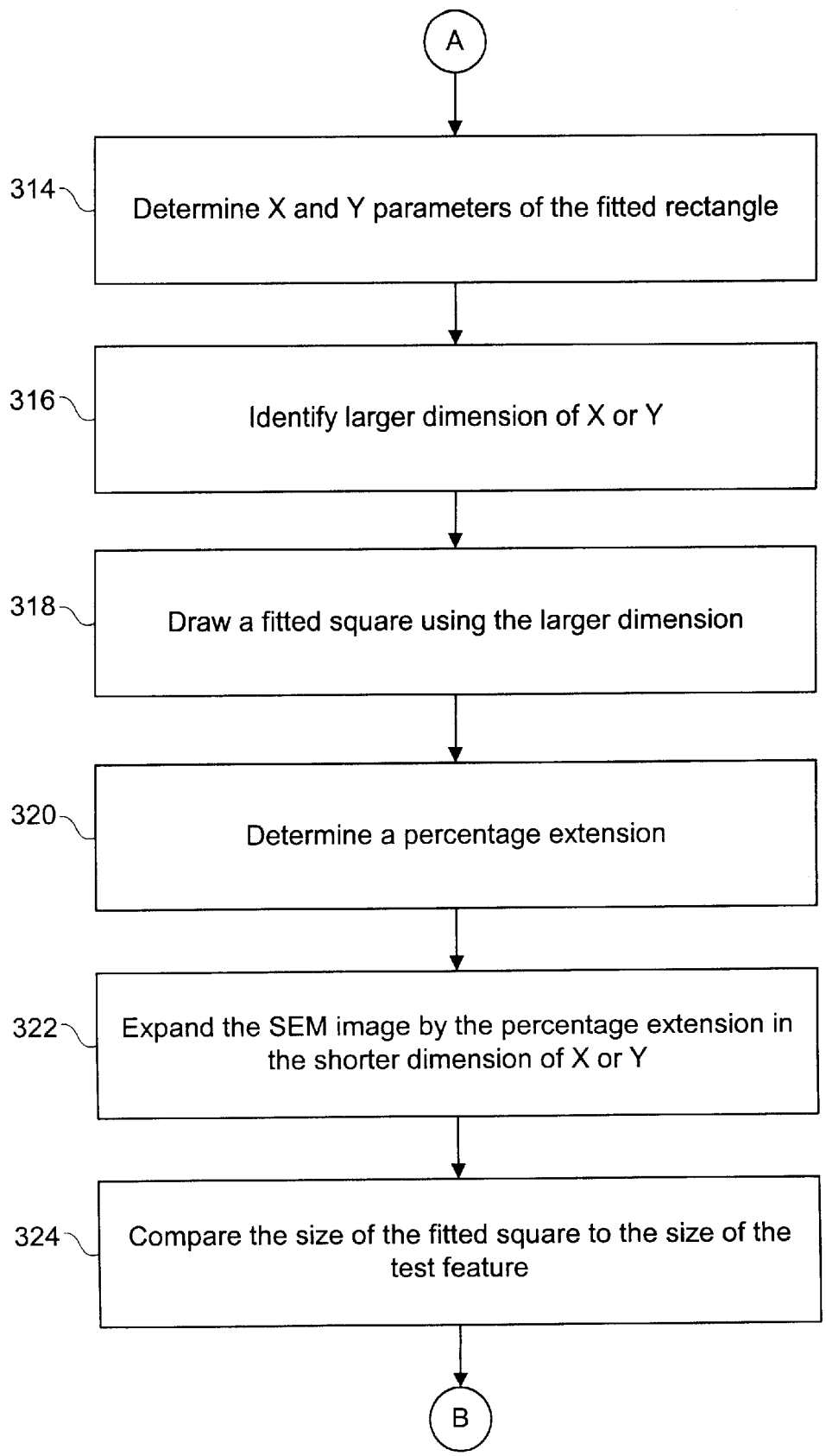
Figure 2C:
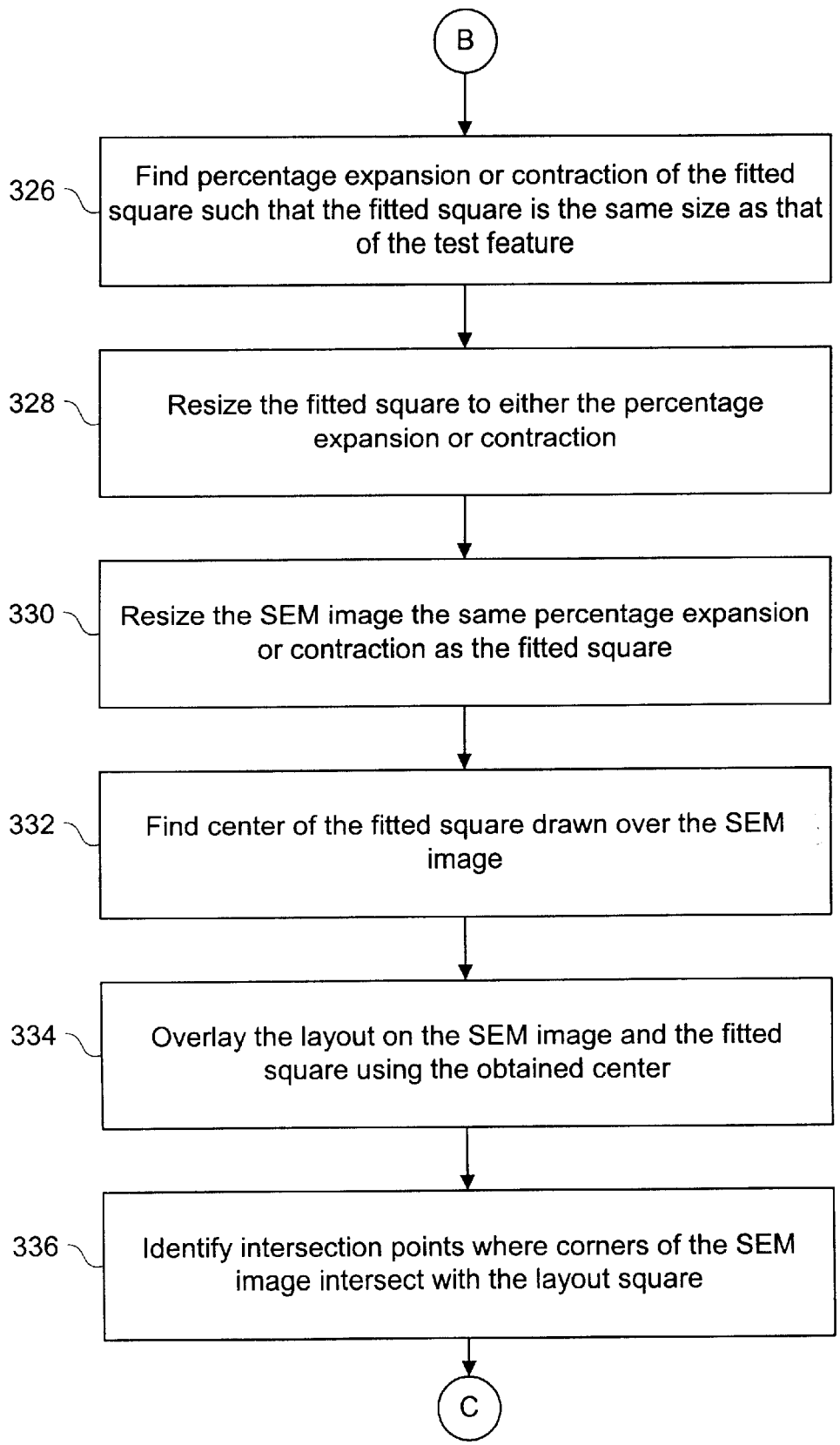
Figure 2D:
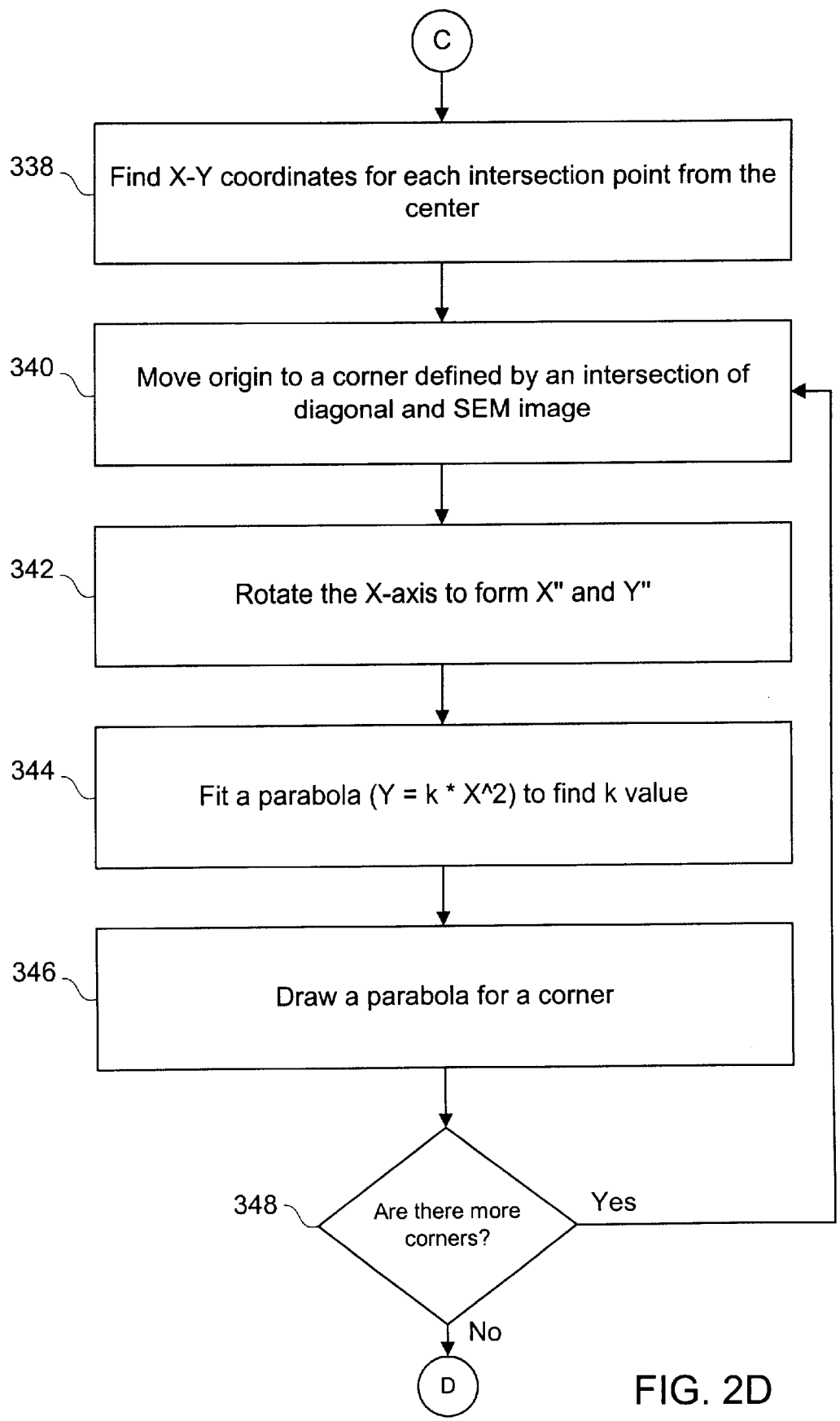

FIGS. 2A–2E are flowcharts that will be described in conjunction with other diagrams to illustrate the methods and computer implemented methods of the present invention. Accordingly, reference is first drawn to FIG. 2A, which is a flowchart 300 showing an operation for inspecting features on a reticle in accordance with one embodiment of the present invention. In operation 302, a test feature 231 having serifs is provided as shown in FIGS. 3A and 3B. In FIG. 3A, a layout square 202 which represents digital data created by a user is shown. FIG. 3B shows the digital representation of layout square 202 with the addition of serifs 204. The layout square 202 and the serifs 204 will be used to determine the quality of features transferred to a reticle. The layout square 202 and serifs 204 guide a user in determining whether or not any irregularities beyond an acceptable limit exist on the surface of the reticle which may inhibit proper formation of patterns on layers of semiconductor wafers.

Figure 4:
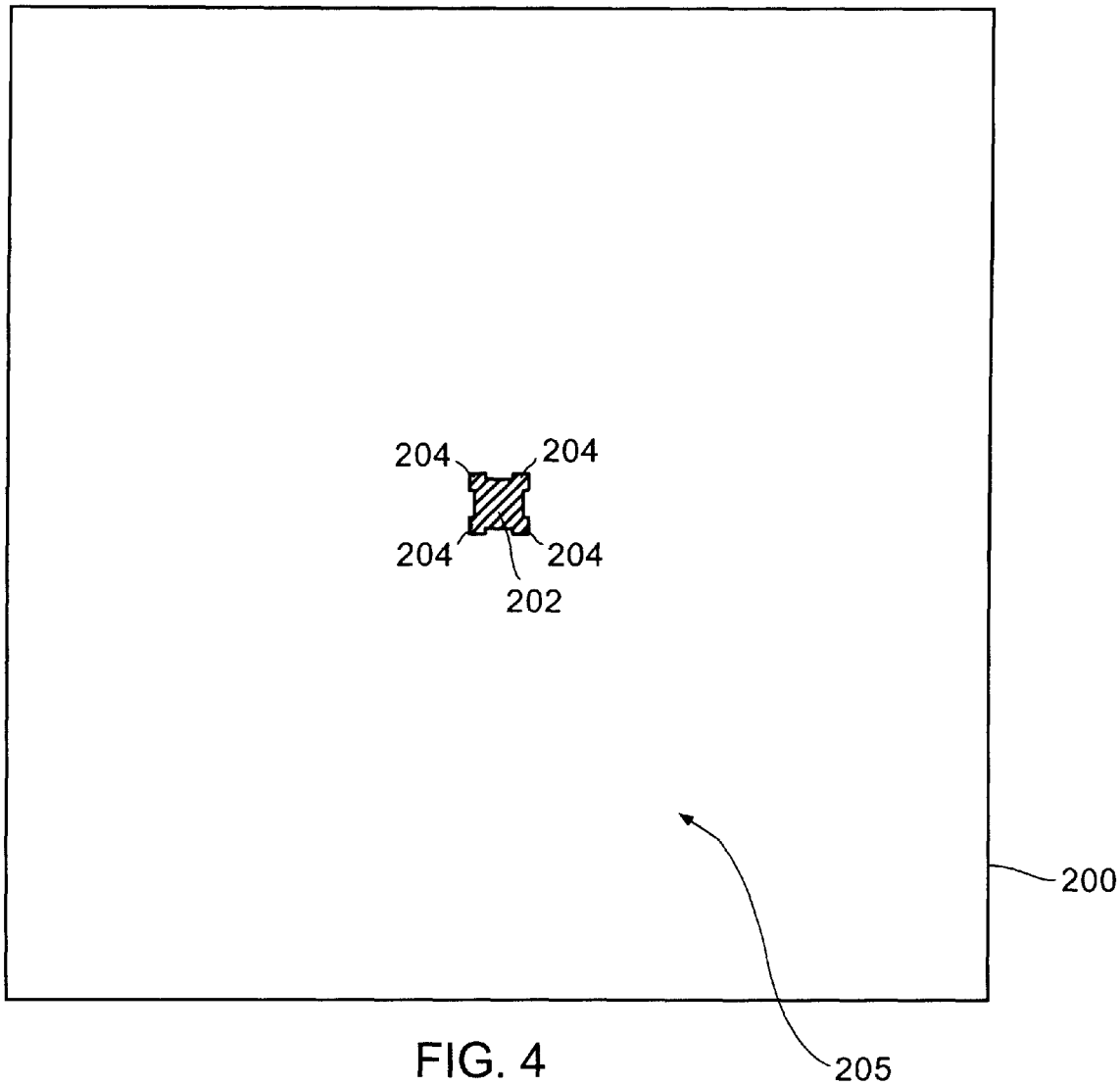
FIG. 4 is one embodiment of the present invention depicting a test feature having serifs transferred to a reticle.

The layout square 202 and the serifs 204 are transferred to a reticle 200 in operation 304 as shown in FIG. 4. The digital data of the layout square 202 and the serifs 204 can be transferred to the reticle 200 using any number of techniques, including applying a layer of chromium onto the reticle 200 and then etching the chromium layer to form the layout square 202 and the serifs 204. The layout square 202 and the serifs 204 may also be transferred to the reticle 200 using a laser tool. Still further, the transferring of the layout square 202 and the serifs 204 can be implemented using a laser or e-beam writing tool. The laser or e-beam writing tool can be used to expose the layout square 202 and serifs 204 in photoresist that is formed on the reticle 200. Then, a development operation can be performed to remove the exposed photoresist so that the remaining photoresist can be used as a mask for etching (e.g., dry or wet). The photoresist can then be stripped, thus defining the layout square 202 and serifs 204. It should be noted that rounding can occur during etching due to the defining of the photoresist and also due to the etching.

Figure 5:
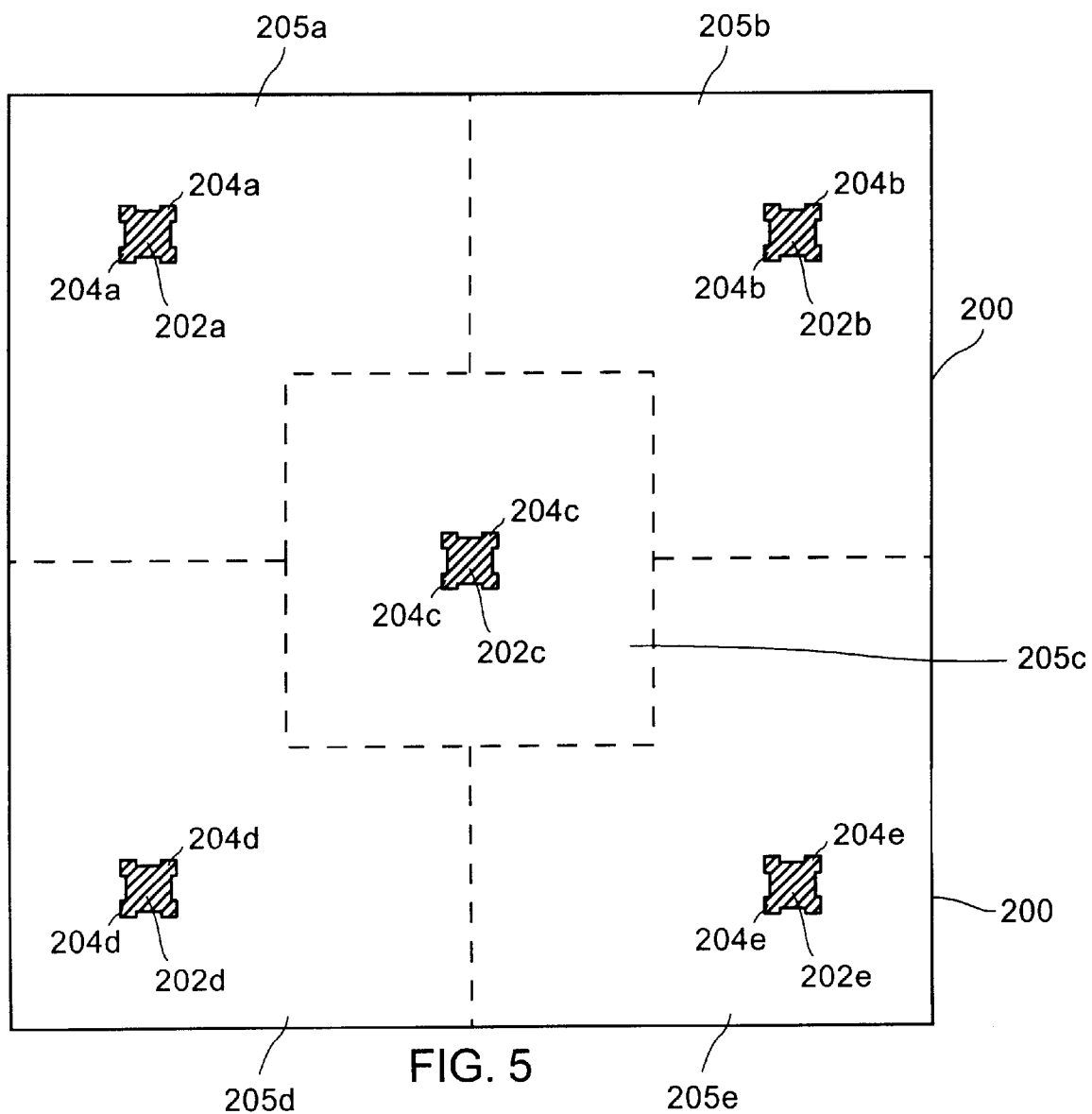
FIG. 5 is another embodiment of the present invention showing various test regions.

To test different locations of the reticle glass, the layout square 202 and the serifs 204 can be formed in test regions 205 as shown in FIG. 4 and 205A–205E as shown in FIG. 5. FIG. 5 is another embodiment of the present invention showing various test regions 205A through 205E. The layout square 202A–202E and the serifs 204A–204E are placed on various test regions 205A through 205E to account for variances in the glass of the reticle 200. As is well known, a reticle may have varying irregularities located throughout the surface. These irregularities may include a number of things, such as contaminants located on the surface of the reticle to varying concavities. In order to account for different irregularities (as well as the development process) located throughout the reticle, the test features 202A–202E are placed on different test regions 205A–205E throughout the reticle 200.

Figure 6:
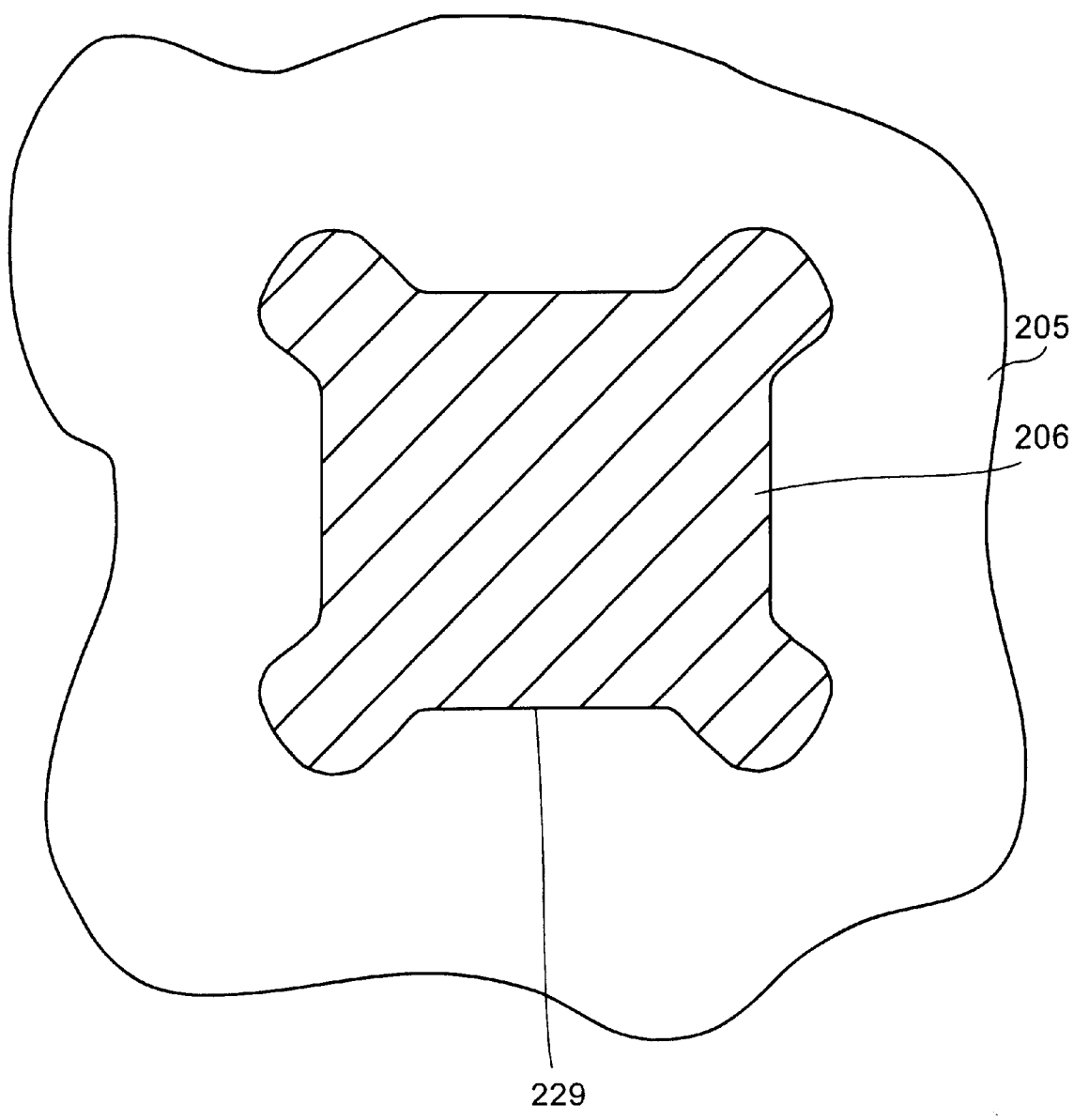
FIG. 6 shows a scanning electron microscope image (SEM) of a test pattern area in accordance with one embodiment of the present invention.

After the digital data of the layout design is transferred to the reticle 200, the reticle 200 is processed by a scanning electron microscope in order to obtain a scanning electron microscope (SEM) image of a test pattern in operation 306. FIG. 6 shows a scanning electron microscope (SEM) image 206 of a test pattern area 205 in accordance with one embodiment of the present invention. The SEM image 206 is a captured image of the test pattern 202 with serifs as they appear on the reticle 200 after the digital data with the serif 204 and test pattern 202 is transferred to the reticle 200. The SEM image may be imported into any number of software tools using a variety of methods. By way of example, the SEM image may brought into a software program in a JPEG format. As is well known, when digital data is transferred to a reticle, there will be some distortions which are often identified by rounding of corners. The rounding effects occur due to optical proximity effects and the small scale of digital data. As can be seen in FIG. 6, the serifs are different in shape than the digital data representation of serifs 204.

After the SEM image is obtained, a preliminary metric, MI, is performed in operation 308 to determine the quality of the SEM image. The preliminary metric measures the difference in area between the layout square 202 and the serifs 204 and the SEM image 206. Then, in operation 310, a determination is made as to whether or not the image transfer is within an acceptable range. This determination is made by comparing the difference in areas. The acceptable range is user defined each time a reticle mask is designed. For purposes of example only, a user may decide that the area of the test feature SEM image must not deviate more than five percent from the area of the test feature in layout design. If the method determines that the deviation in the SEM image test feature area and the layout design test feature area is greater than five percent, the method will determine that the reticle is unacceptable.

If the image transfer is not within an acceptable range, measures should be taken to determine why the image transfer is hot within an acceptable range. For example, the layout design and the processing of the layout design should be checked. In addition, the processing (e.g., fabrication) of the layout design, for example, transferring the layout design to the reticle should also be checked. The tools used to transfer the digital data to the reticle may also cause the image transfer to be unacceptable. For example, the application (e.g., sputtering) technique used to deposit the chromium onto the reticle, or the laser tool which is used to transfer the digital data onto the reticle may not properly transfer the image to the reticle, thereby causing the transferred image to fall outside the acceptable range. If the image transfer is not within an acceptable range, the flowchart reverts back to operation 302. Operations 302 through 310 are repeated until the image transfer is within an acceptable range as shown in operation 310.

Figure 7:
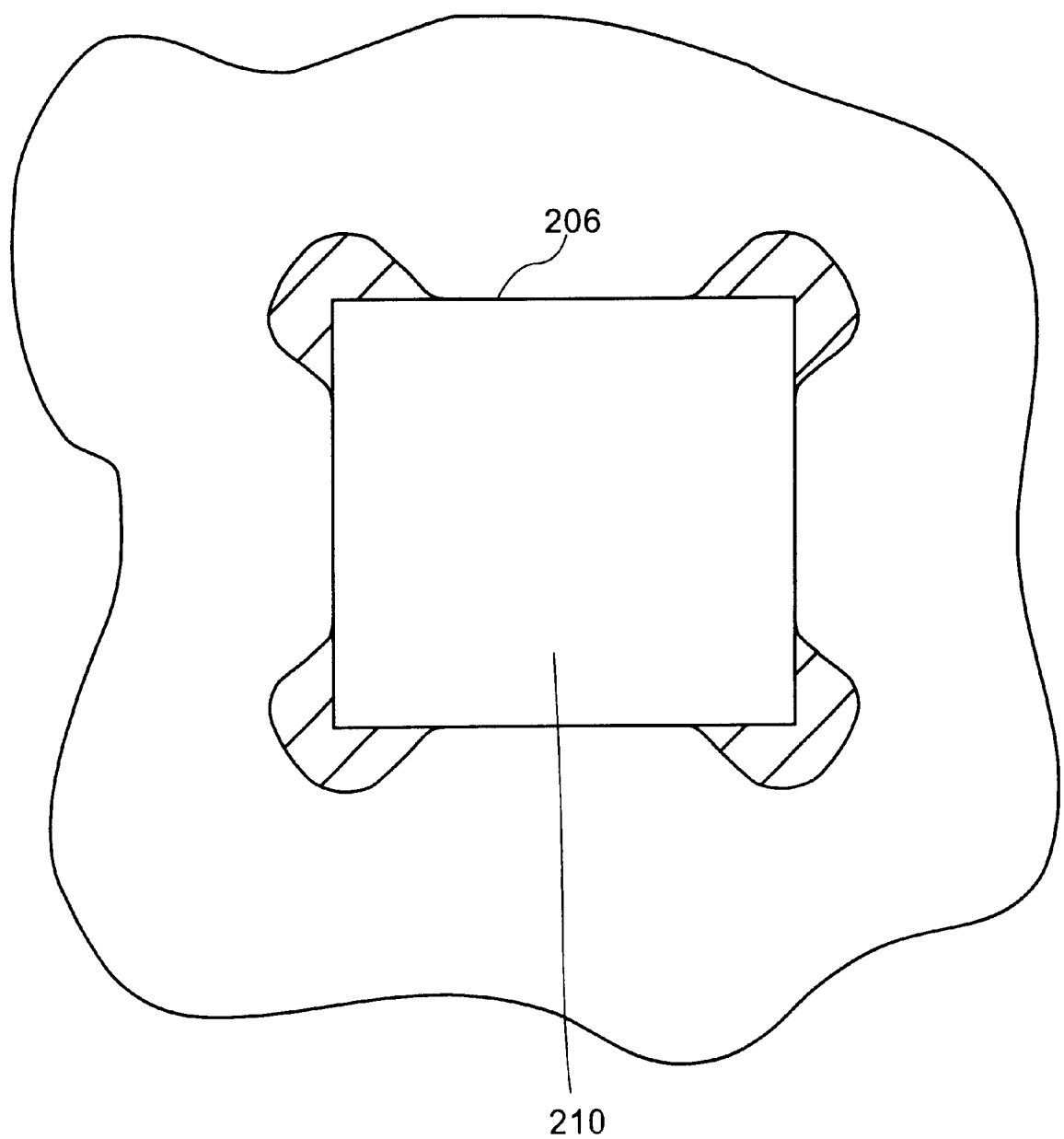
FIG. 7 shows a fitted rectangle drawn onto the SEM image in accordance with one embodiment of the present invention.

Referring back to FIG. 2A in operation 310, if it is determined that the image transfer falls within an acceptable range, the method moves to operation 312. In operation 312, a fitted rectangle 210 whose sides fall on straight proportions of the SEM image 206 is drawn onto the SEM image 206 as depicted in FIG. 7. FIG. 7 shows a fitted rectangle 210 drawn into the SEM image 206 in accordance with one embodiment of the present invention. The sides of the fitted rectangle 210 fall onto the sides of the SEM image 206 that define the transferred layout square 202 from the layout design. The fitted rectangle may be drawn onto the SEM image 206 using a variety of software tools capable of allowing a user to impose shapes onto images.

Figure 8B:
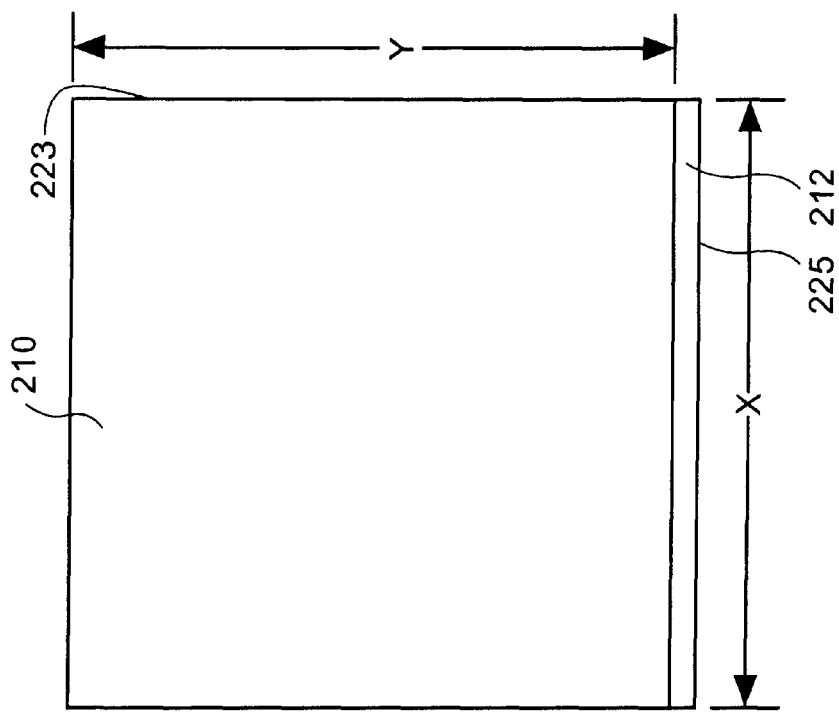
FIG. 8B shows a fitted rectangle with an extension to form a fitted square in accordance with one embodiment of the present invention.
Figure 8A:
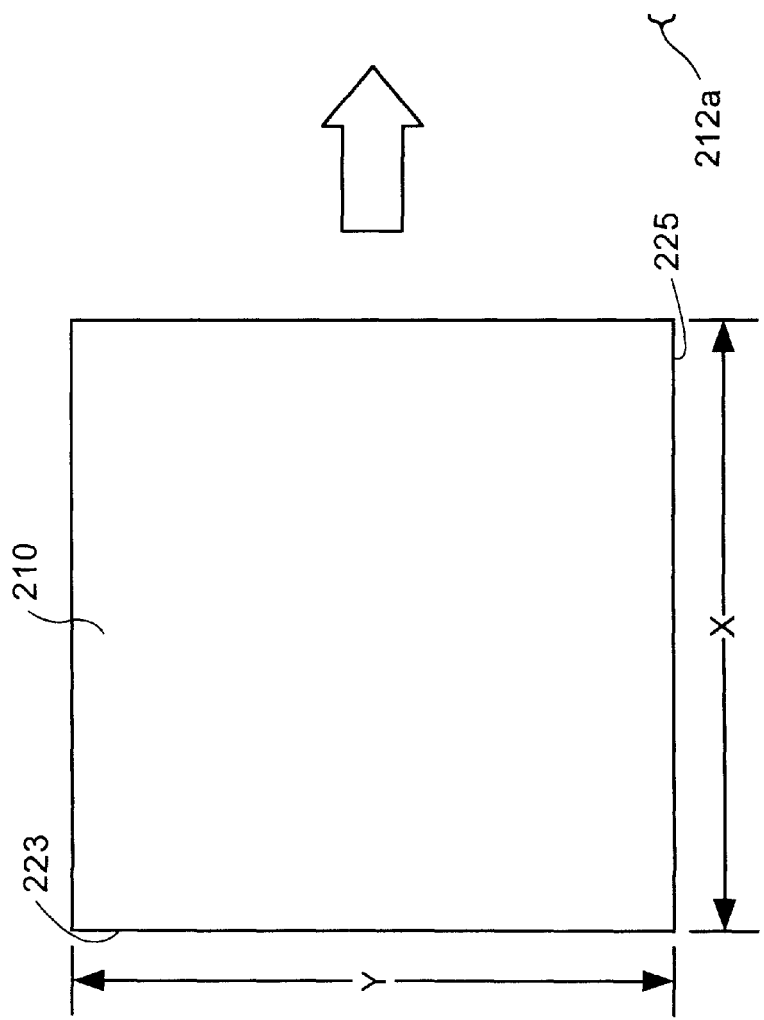
FIG. 8A shows X parameters and Y parameters of a fitted rectangle drawn onto the SEM image in accordance with one embodiment of the present invention.

After the fitted rectangle 210 is drawn onto the test feature 206, the X and Y parameters of the fitted rectangle 210 are determined in operation 314 as shown FIG. 8A. The X parameter 225 and the Y parameter 223 are determined in order to identify which one is larger of the fitted rectangle 210. Meaning, if the X parameter 225 is larger than the Y parameter 223 or the Y parameter 223 is larger than the X parameter 225, as illustrated in operation 316. After a larger parameter is determined, the larger parameter is used to draw a fitted square 214 in operation 318 as shown in FIG.

8B. The X parameter and the Y parameter are determined using a software tool capable of applying numerical coordinates to digital data imported into the software tool.

In the example, the X parameter 225 is larger than the Y parameter 223, therefore, the Y parameter 223 is extended such that the Y parameter 223 is equivalent to the X parameter 225 to form a fitted square 214. As shown in FIG. 8B, an extension 212 is added to the Y parameter 223 in order to create the fitted square 214. The extension 212 is the amount by which the Y parameter 223 is extended in order to make the Y parameter 223 equal in length to the X parameter 225. After the fitted square 214 is created, a percentage extension 212a is determined in operation 320. The percentage extension 212a refers to the percentage by which the shorter parameter is extended in order for the shorter parameter to be equivalent in length to the larger parameter.

Figure 9:
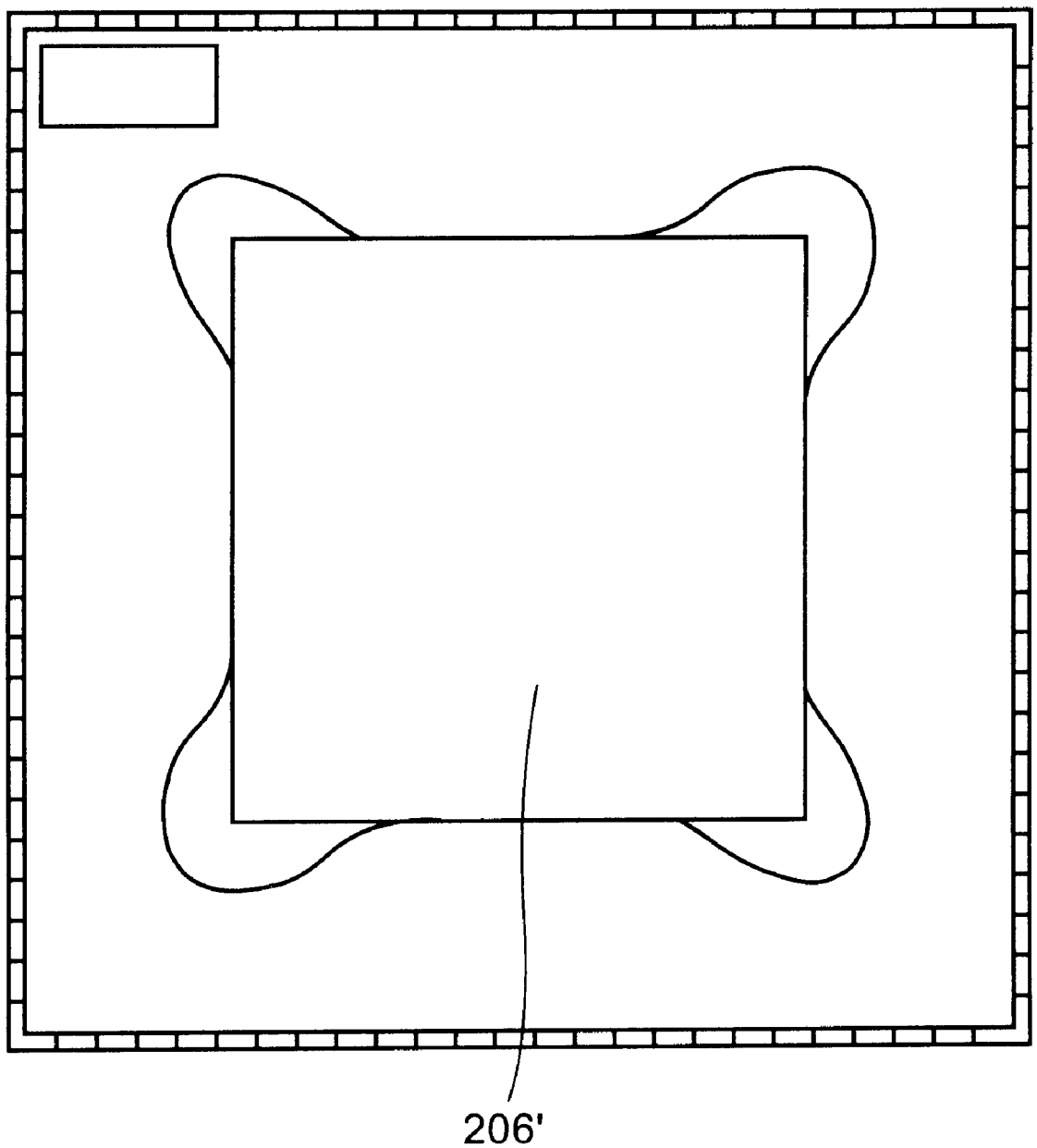
FIG. 9 depicts an expanded SEM image in accordance with one embodiment of the present invention.

After the percentage extension 212a is determined, this value is applied to the SEM image, in operation 322 as shown in FIG. 9. FIG. 9 depicts an expanded SEM image 206' in accordance with one embodiment of the present invention. In operation 322, the SEM image 206 is extended to form SEM image 206' by the percentage extension used to the extend the X parameter 225 or the Y parameter 223 in the fitted rectangle 210. Referring back to our example, the shorter dimension Y was extended by the percentage extension 212a. Therefore, the SEM image 206 is expanded by the same percentage extension to form the SEM image 206'.

Figure 10A:
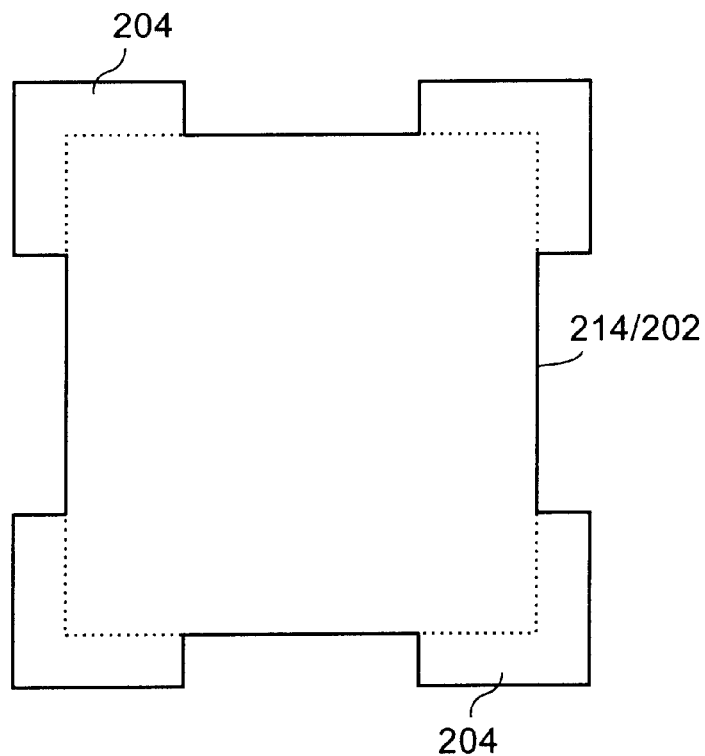
FIG. 10A shows the comparison of the fitted square to the test feature of the layout design.

Once the SEM image 206 is expanded by the percentage extension 212a to form SEM image 206', the fitted square 214 is compared to the layout square 202 of the layout design in operation 324 as shown in FIG. 10A. FIG. 10A shows the comparison of the fitted square 214 to the layout square 202 of the layout design. The fitted square 214 is laid onto the layout square 202 and serifs 204 in order to compare the size of the fitted square 214 with the size of the layout square 202. The fitted square 214 is compared with the layout square 202 in order to find the percentage expansion or contraction of the fitted square in operation 326. The percentage expansion or contraction is the percentage necessary to expand or contract the fitted square 214 such that the fitted square 214 is the same size as the layout square 202. Also shown in FIG. 10A are serifs 204 as shown in FIG. 3B.

Figure 10B:
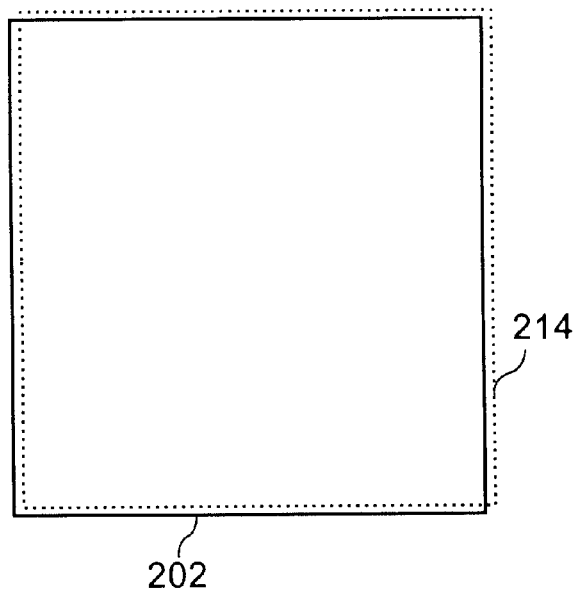
FIG. 10B is an offset view of the fitted square over the layout square illustrating the same size of the fitted square and the layout square in accordance with one embodiment of the present invention.

Referring back to the example, the fitted square 214 in this case is the same size as the layout square 202. As can be seen, the layout square 202 is completely covered by the fitted square 214, as such, only the fitted square 214 is visible in FIG. 10A. FIG. 10B is an offset view of the fitted square 214 over the layout square 202 depicting the same size of fitted square 214 and the layout square 202. However, it should be noted that in most other situations, the fitted square 214 and the layout square 202 will not be the same size. Instead, the fitted square 214 may be larger or smaller than the layout square 202 depending on any losses or gains during the transfer of the layout square 202 of the layout design to the reticle 200.

Still referring to FIG. 10A, after the test feature 214 of the SEM image 206' is compared to the layout square 202 of the layout design, a percentage expansion or contraction of the fitted square 214 is found in operation 326. The percentage expansion found allows the fitted square 214 to be equivalent in size to the layout square 202. For example, in some situations, the fitted square 214 will be larger in size than the layout square 202. In these cases, a percentage contraction is determined in order to contract the fitted square 214 by the percentage contraction in order for the fitted square 214 to be equivalent in size to the layout square 202. Also, in other situations, the fitted square 214 may be smaller than the layout square 202. In this situation, a percentage expansion is determined so that the fitted square 214 may be expanded by the percentage expansion such that the fitted square 214 will be equivalent in size to the layout square 202. In this example, the fitted square 214 and the layout square 202 are equivalent in size. Therefore, the percentage expansion and contraction required is zero.

After the percentage expansion or contraction is found, the fitted square 214 must be resized to either the percentage expansion or contraction in operation 328 to form fitted square 214'. In this example, as mentioned above, the percentage expansion was found to be zero since the fitted square 214 and layout square 212 were the same size. Therefore the fitted square 214', which was resized by the percentage expansion, is the same size as fitted square 214.

Once the fitted square 214 is resized, the SEM image 206' is also resized by the same percentage expansion or contraction as the fitted square in operation 330. If the fitted square 214 was smaller than the layout square 202 and required a percentage expansion, then the SEM image 206' is expanded by the percentage expansion. On the other hand, if the fitted square 214 was larger than the layout square 202, then the SEM image 206' is contracted by the percentage contraction. In this example, the SEM image 206" was expanded to form SEM image 206" (of FIG. 11) by the same percentage expansion as the fitted square 214, which in this case was zero. As such the SEM image 206" is the same size as the SEM image 206'. It should be noted that the operations which expand or contract the fitted square 214 and the SEM image 206' may be completed by a software tool having a resizing function.

Figure 11:
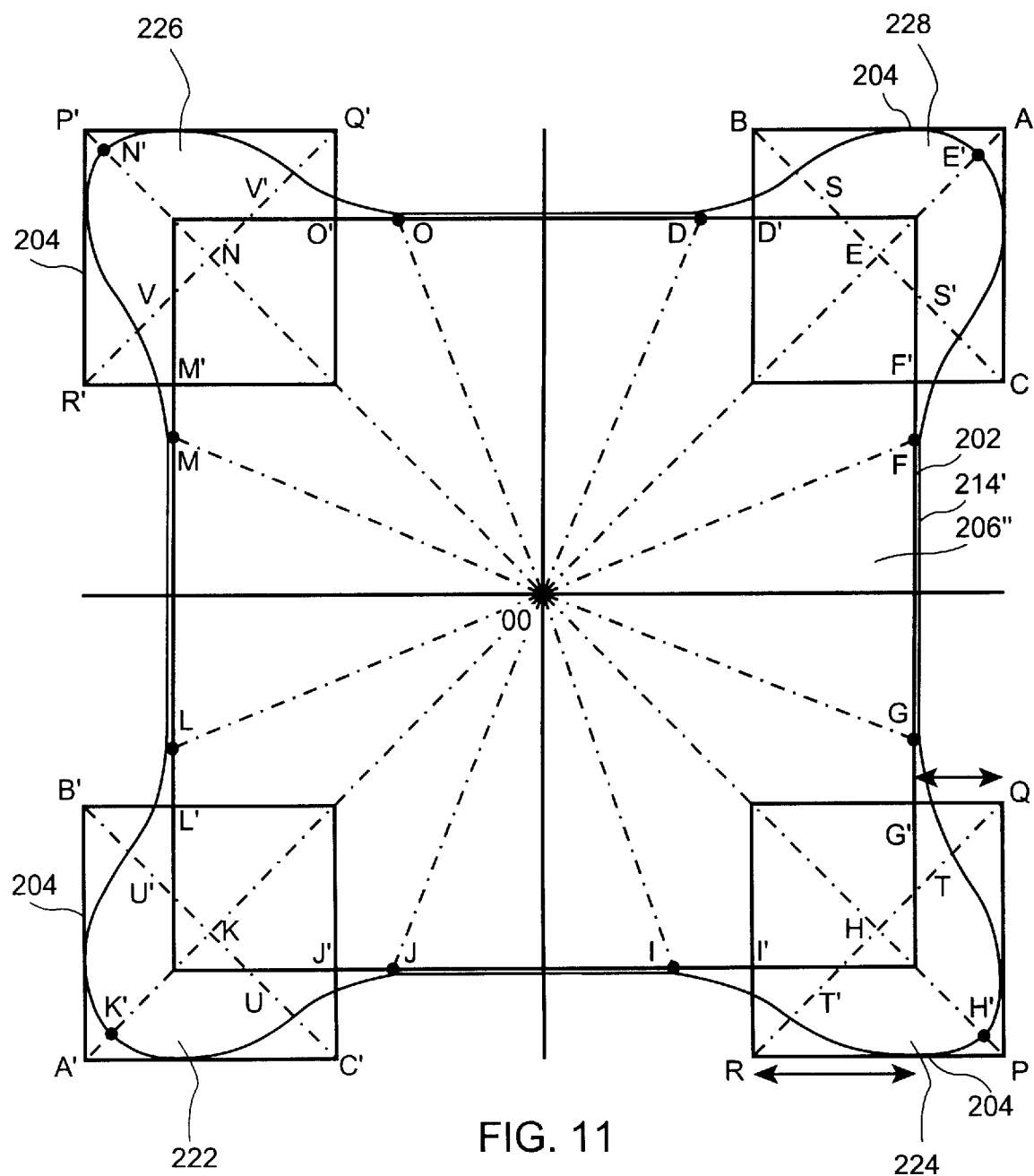
FIG. 11 shows the center of the fitted square drawn in the SEM image, in accordance with one embodiment of the present invention.

After the SEM image 206" and the fitted square 214' are resized to be equivalent to the layout square 202, the center of the fitted square 214' is drawn over the SEM image 206" in operation 332, as shown in FIG. 11. FIG. 11 shows the center of the fitted square 214' drawn in the SEM image 206", in accordance with one embodiment of the present invention. The center of the fitted square 214' is denoted in FIG. 11 by the point 0,0. Once the center of the fitted square 214' is found, operation 334 is performed.

In operation 334, the layout square 202 and the serifs 204 are overlaid on the SEM image 206" and the fitted square 214' by importing the layout square 202 and the serifs 204 into a software tool capable of applying numerical values to JPEG formatted images. The layout square 202 is laid over the fitted square 214' and the SEM image 206" such that the center of the layout square 202 is directly over the center of the fitted square 214'. The serifs 204 are laid over the SEM image 206" in order to determine how accurately the serifs 204 were reproduced on the reticle 200, as will be further discussed below. The images of the serifs 204, as they were formed on the reticle 200, are depicted by the corners 222, 224, 226 and 228. Referring back to the example, the center of the layout square 202 lies directly over the center 0,0 of the fitted square 214'. However, again it should be noted that the fitted square 214' and the layout square 202 are the same size. Thus, the fitted square 214' and the layout square 202' are seen one on top of each other.

When the layout square 202 is laid over the fitted square 214', intersection points of where the corners 222, 224, 226 and 228 intersect with the layout square 202 are determined in operation 336. In addition, the top most point of the corners 222, 224, 226 and 228 are identified in operation 336. The top most point of each corner is the point in each corner which is furthest from the origin O,O to the fitted square 214'. Referring back to the example, the intersection points where the corner 222 intersects the layout square 202 are intersection points L and J. The top most point of the corner 222 is point K'. The intersection points where the corner 224 intersects the layout square 202 are intersection points I and G. The top most point of the corner 224 is point H'. The intersection points where the corner 226 intersects the layout square 202 are intersection points M and O. The top most point of corner 226 is point N'. The intersection points where the corner 228 intersects the layout square 202 are intersection points D and F. The top most point of corner 228 is point E'. Once the intersection points for the corners 222, 224, 226 and 228 and the top most points K', H', N' and E' are identified, the coordinates for each point is determined. The intersection points M, L, J, I, G, F, D, and O, and the top points K', H', N' and E' are identified in order to determine the accuracy of the serifs 204 used in the layout design for the test feature. The accuracy of the serifs 204 aids in determining the acceptability of the reticle, as will be further discussed below.

Once the intersection points M, L, J, I, G, F, D and O and the top most points E', H', K' and N' are determined, the X-Y coordinates of the intersection points are found in operation 338. The X-Y coordinates are determined with respect to the origin O,O found in operation 332. Again, these coordinates may be ascertained using any software tool capable of applying numerical values to JPEG formatted images.

After the X-Y coordinates for the intersection points are found in operation 338, the origin of the layout square 202 and the fitted square 214' is moved to a corner of the SEM image 206" in operation 340. The moved origin (e.g., defined at X' and Y') is defined at an intersection of a diagonal which extends from the original origin O,O to the top most point of the corner of the SEM image. Referring back to the original example, an origin is moved to the corner 228. The moved origin is defined at point E', as shown in FIG. 12.

Once the origin is moved from point 0,0 of the fitted square 214' and the layout square 202 to the point E' of the corner 228 of the SEM image 206", the X axis and the Y-axis are rotated to define X" axis and Y" axis in operation 342. In our example, the X and Y axis are rotated such that the positive Y" axis is along the diagonal which extends from the point O,O to the top point A in corner A, and the X" axis is parallel to a diagonal that extends between point C of serif 204 to point B of serif 204.

A parabola is fit onto to the new coordinate system defined by the X" axis and the Y" axis after the rotation is complete in operation 344. The parabola is fit into an area defined by the serif 204 of the layout design and a corner of the SEM image 206". The parabola is defined using the equation Y=k*X². This equation is used to find an average k value. The k value is found by rotational transform values for X" and Y", or the points where the serif corners of the SEM image 206" intersect with the layout square 202 in the new coordinate system defined by the X" axis and the Y" axis. When the average k value is found, the parabola is defined according to the X" axis and the Y" axis. In the example, a parabola 207 was fit in the corner 228 of the SEM image 206" at point E' within the serif 204 of the layout design. The X" and Y" values used to obtain the average k value were rotational transform values for the point D and the point F, the points where the corners of the SEM image 206' intersect with the layout square 202. The parabola 207 is shown for the corner 228 of the SEM image 206 in FIG. 12.

Figure 12:
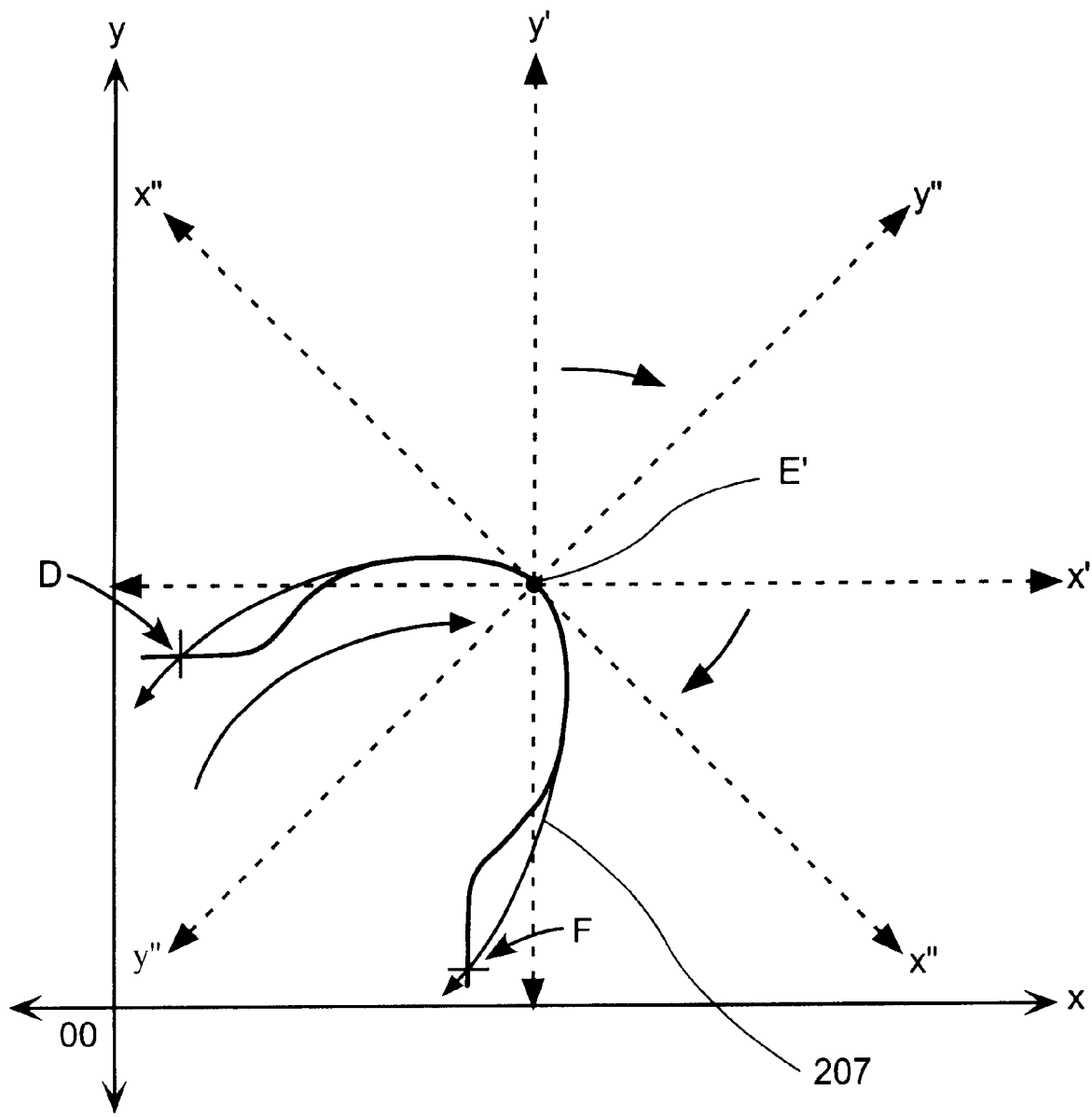
FIG. 12 shows a parabola drawn for the corner of the SEM image, in accordance with an embodiment of the present invention.

FIG. 12 shows a parabola drawn for the corner 228 of the SEM image 206, in accordance with an embodiment of the present invention. The parabola 207 intersects with the fitted square 214' and the layout design square 202 at the intersection points D and F as shown. The intersection points D and F were found in operation 336 and define where the corner 228 of the SEM image 206" intersects with the layout square 202 and the fitted square 214'.

Figure 13:
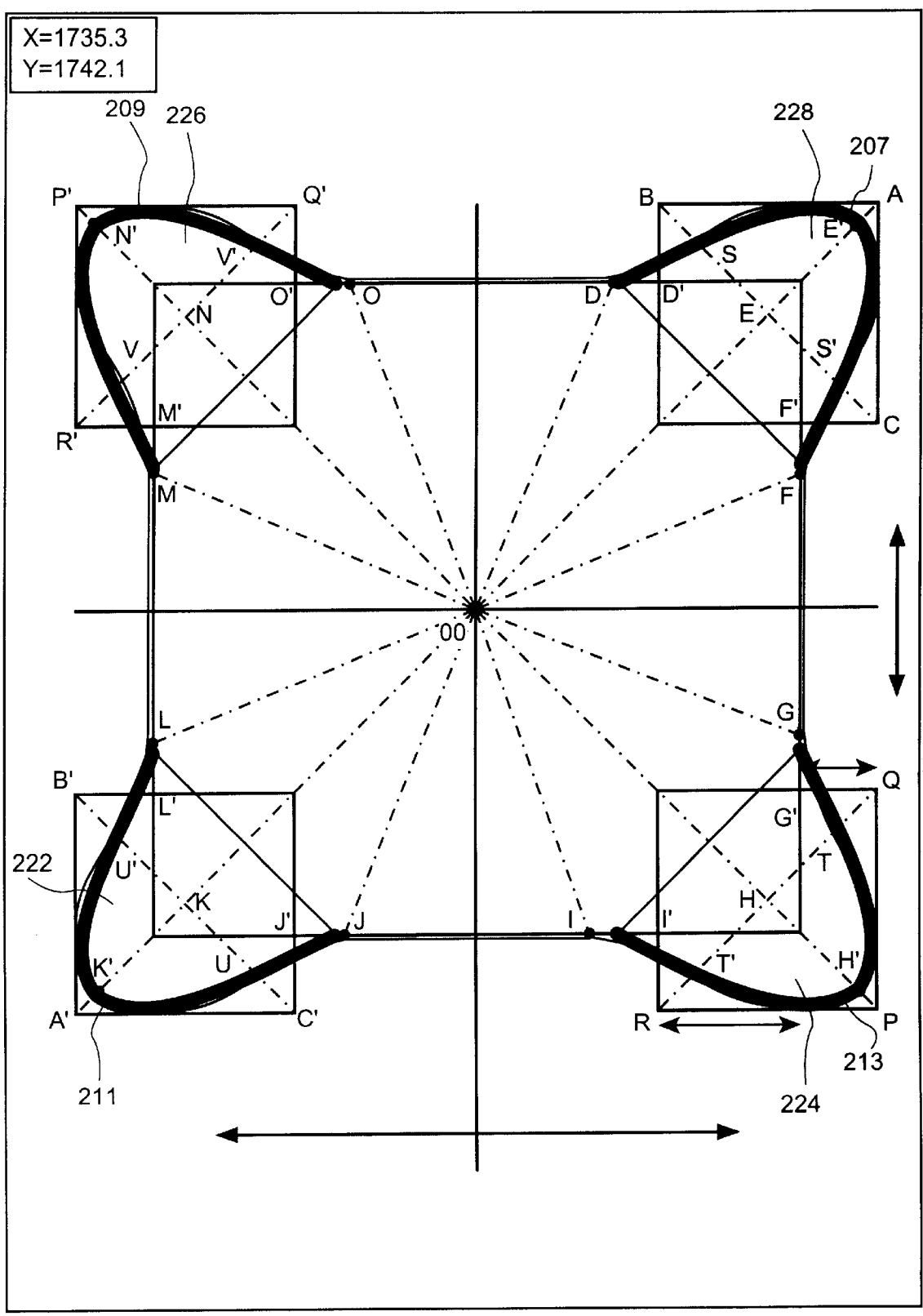
FIG. 13 shows the SEM image fitted with parabolas in corners, in accordance with one embodiment of the present invention.

A determination is then made after the parabola is drawn for the corner as to whether or not there are more corners in operation 348. If there are more corners, the operation 348 will revert back to operation 340 as shown in FIG. 2D. Referring back to the example, operations 340 through operations 348 will be performed to form parabolas 209, 211, and 213, as shown in FIG. 13. FIG. 13 shows the SEM image 206 fitted with the parabolas 209, 211 and 213 in the corners 226, 222 and 224.

FIG. 13 shows the SEM image 206" with the fitted parabolas 207, 209, 211 and 213 in the corners 222, 224, 226 and 228 of the SEM image 206", in accordance with one embodiment of the present invention. After the parabolas 207, 209, 211 and 213 are formed on the SEM image 206", a diagonal difference between the layout and the SEM image 206" is determined. The diagonal difference is a second metric, M2, which is used to determine the accuracy of image reproduction on the reticle 200. A pass or fail is then ascertained in operation 350. The diagonal difference in operation 350 is the difference between the top most point of the corner, and the far corner of the serif of the layout design. In this example, referring to the parabolas 207 and 211 and the corners 228 and 222 in FIG. 13, the diagonal difference is the difference between a diagonal defined between the point E' to point K' and a diagonal defined between the point A' to point A. After the diagonal difference is determined, a pass or fail is ascertained. Again, the pass or fail threshold is user defined and is determined on a case by case basis. For purposes of example only, a user may decide a deviation not greater than five percent is an acceptable amount. If the diagonal defined from point E to point A has a unit length of twenty, then the length of the diagonal defined between point E and E' would need a unit length falling in between 19 and 21 in order to pass. The same procedure will be repeated for the parabolas 209 and 213, in the corners 226 and 224 in operation 350.

Figure 2E:
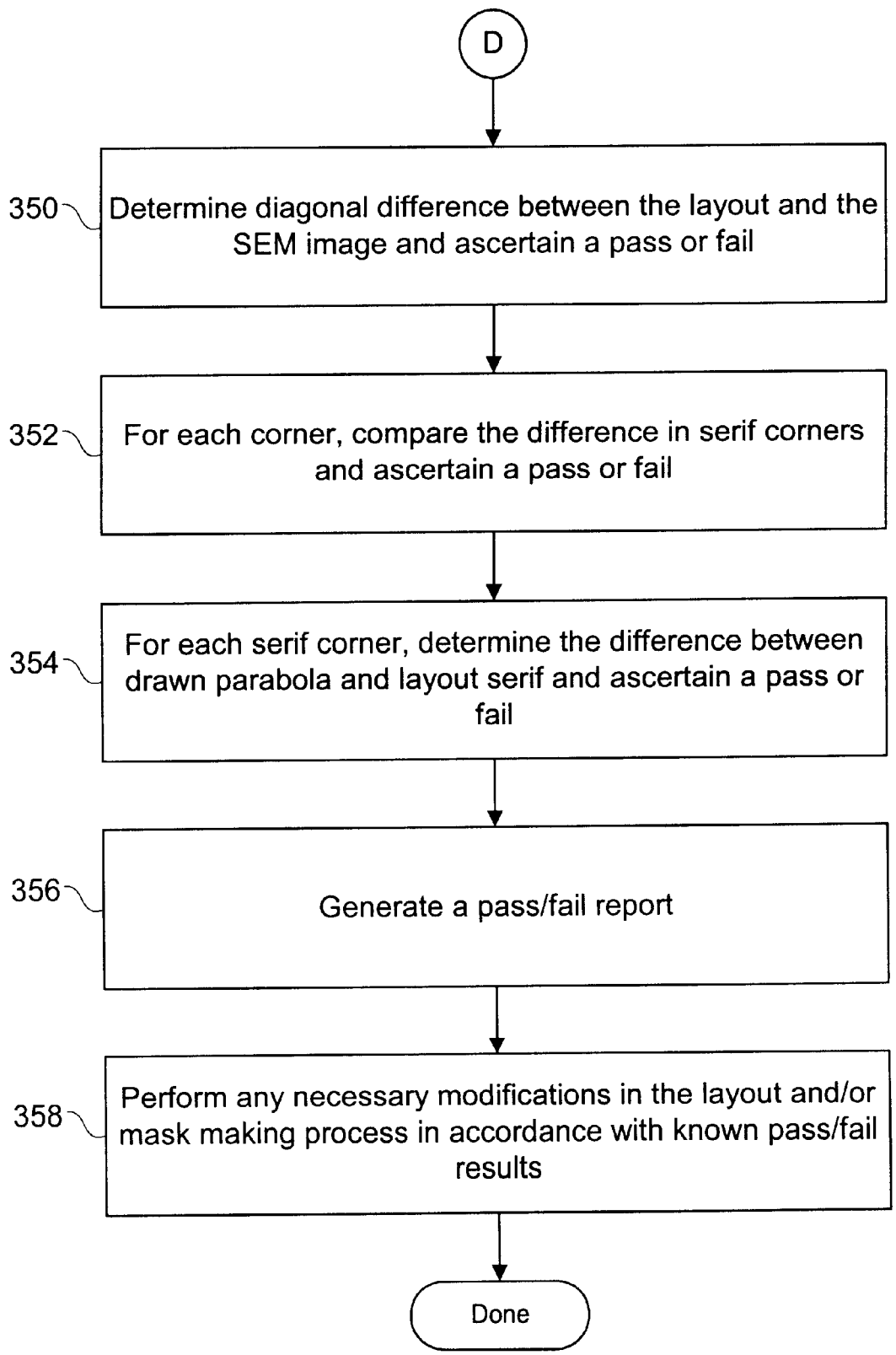
Figure 3B:
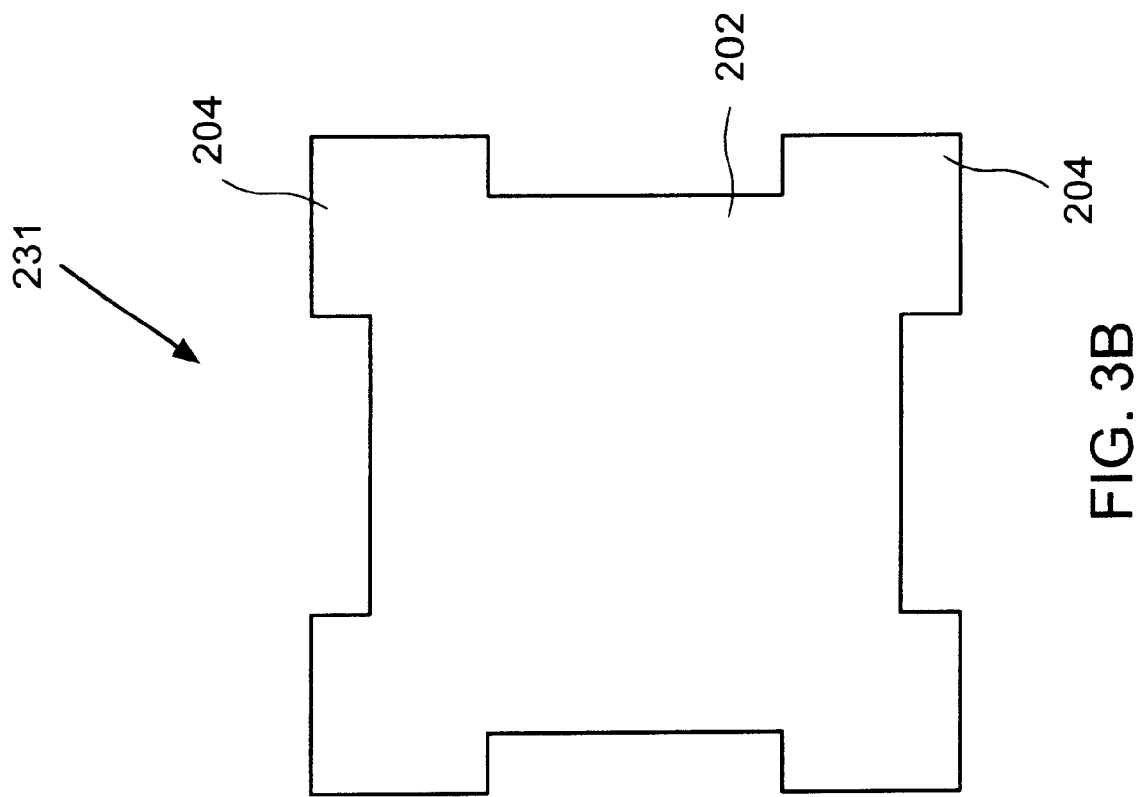
FIG. 3B shows the digital representation of a test feature with the addition of serifs in accordance with one embodiment of the invention.
Figure 3A:
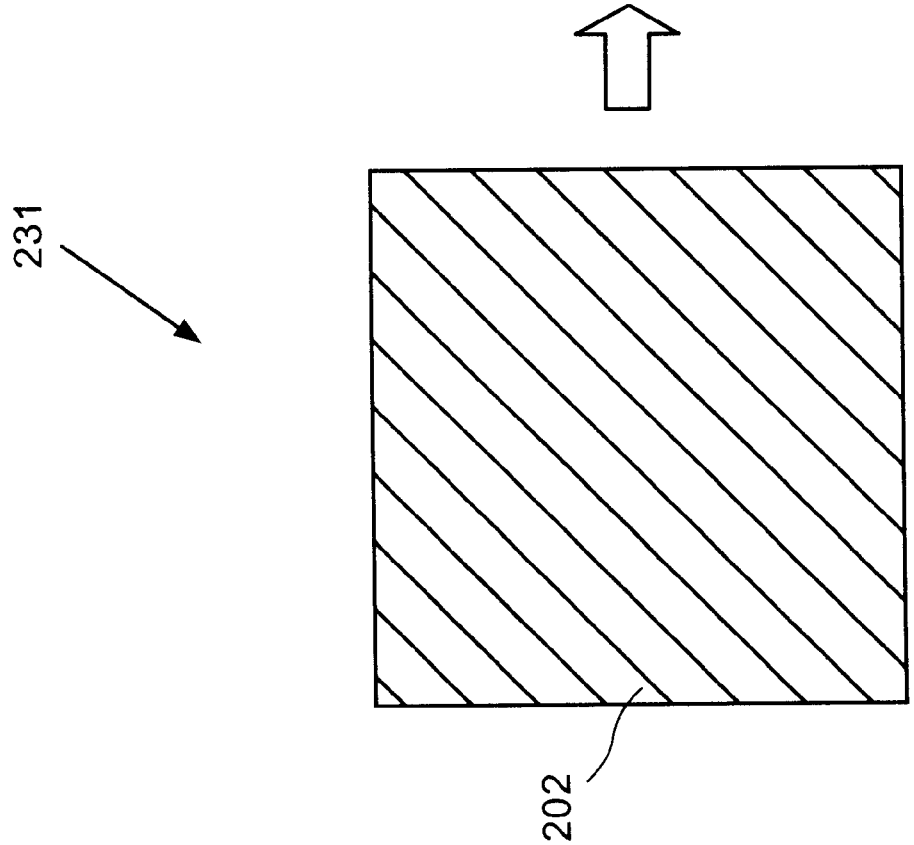
FIG. 3A shows the digital representation of a feature inputted by a user in accordance with one embodiment of the present invention.
Figure 14:
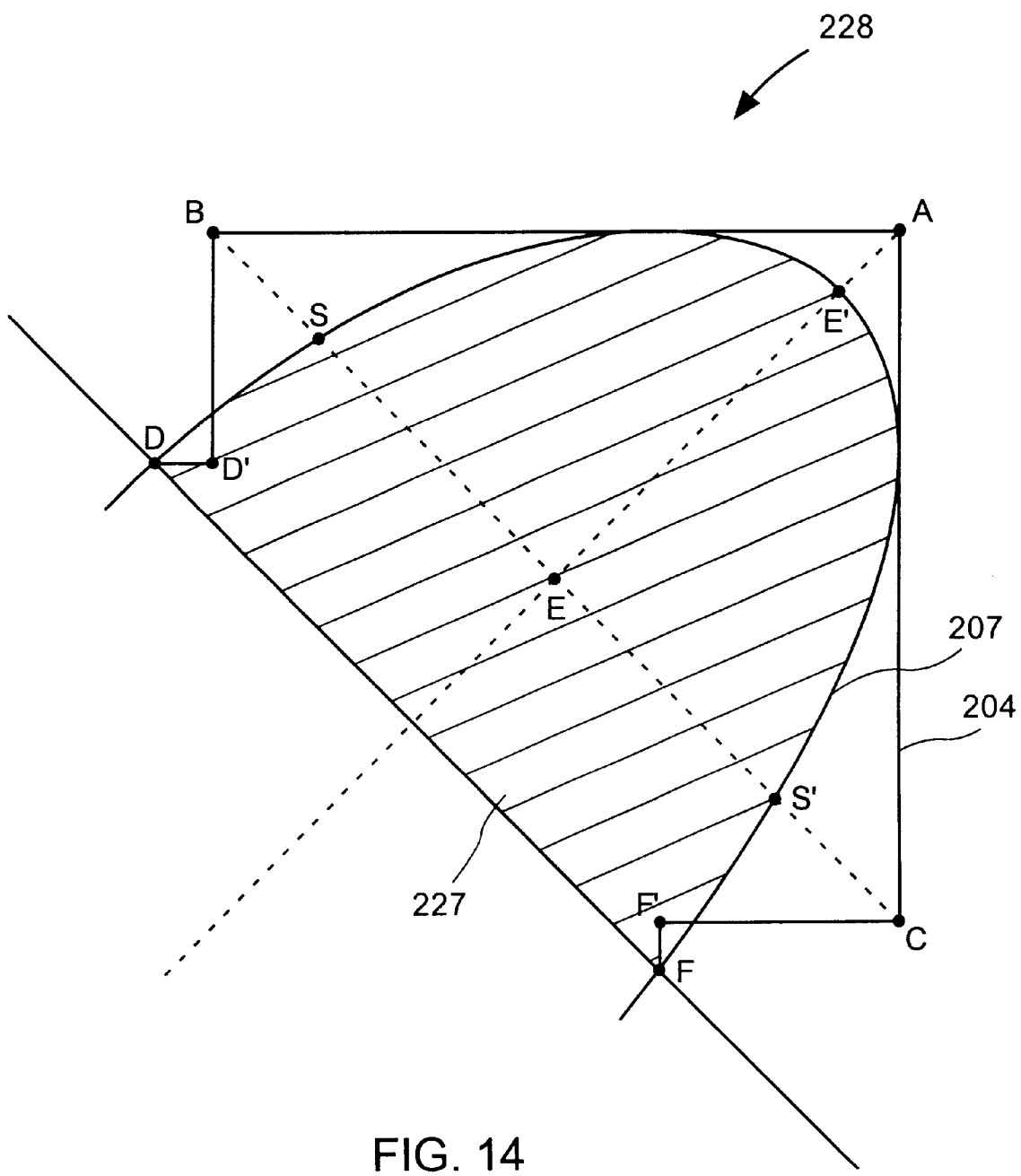
FIG. 14 is a magnified view of a corner having three serif corners defined by points A, B and C, in accordance with one embodiment of the present invention.

Still referring to FIG. 2E and the flowchart contained therein, after the operation 350 is completed, the method moves to operation 352. In operation 352, a third metric, M3, is determined. The third metric is the difference in serif corners for each corner. A pass or fail is then ascertained with respect to each corner. Making reference to FIG. 14, which is a magnified view of corner 228, the corner 228 has three serif corners defined by points A, B and C. The difference in serif corners is taken for the serif corner at point B by measuring the difference in a diagonal defined between the point E and point B and a diagonal defined between the point E and a point S. This procedure is repeated for the serif corner at point A and the serif corner at point C. A pass or fail is then ascertained based on the found difference. The criterion for passing or failing is user determined on a case by case basis. For example, a user may decide that the difference in serif corners may not deviate by more than ten percent. If the difference varies by more than ten percent, then the serif metric has failed the third metric. Operation 352 also performs the third metric for the corners 222, 224 and 226.

In operation 354, a fourth metric, M4, is determined. The fourth metric is a determination of the difference in area between the drawn parabola and the layout serif. The metric is found by comparing the areas of the drawn parabola with the area of the layout serif. After the comparison, a pass or fail is ascertained. Referring again to the example in FIG. 14, the area 227 of the parabola 207 is defined by the parabola 207 which is bounded by a diagonal defined between the point D and the point F. The layout serif area referred to in operation 354 is the area of the serif which is bounded by diagonals formed between the following points the point D to point D', the point D' to the point B, the point B to the point A, the point A to the point C, the point C to point F', the point F' to the point F and finally by a diagonal defined between the point F and the point D. The difference in area between the layout serif and the parabola 207 is then determined, and a pass or fail is then ascertained. Again, the pass or fail threshold is determined by a user on a case by case basis. Once the pass or fail is determined for the corner 228, the operation will proceed to make determinations for the corners 222, 224 and 226.

Figure 15:
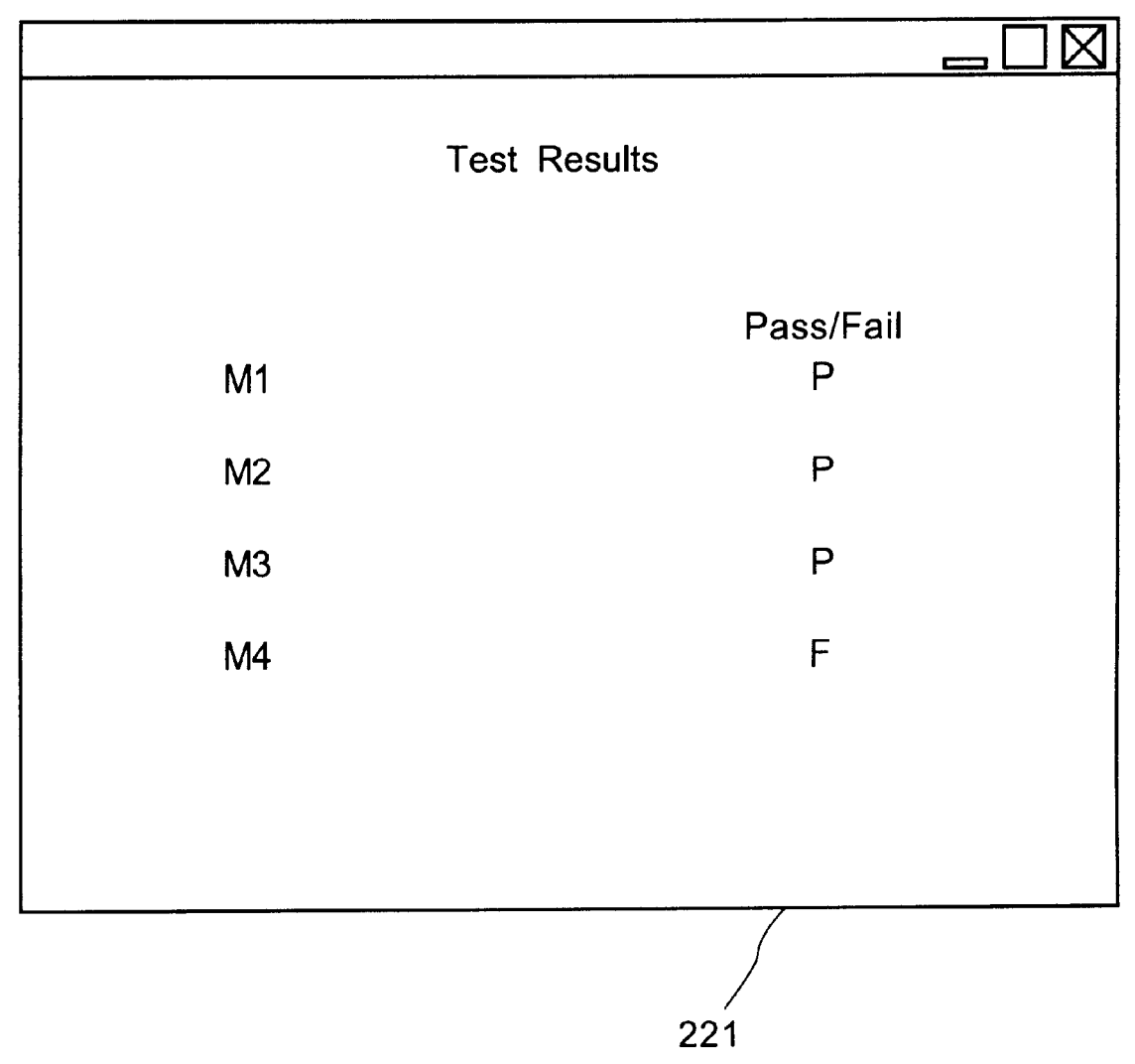

The pass or fails found in the first, second, third and fourth metric will be reflected in a report generated in operation 356 as shown in FIG. 15. FIG. 15 shows a pass or fail report 221 generated in operation 356 in accordance with the embodiment of the present invention. As shown in FIG. 15, the pass or fail report 221 shows which metric was performed, and the results indicating whether a pass or fail was achieved for that metric. To summarize, the first metric, M1, was performed in operation 308. The second metric, M2, was performed in operation 350 when the diagonal difference between the layout serif and the SEM image was determined. The third metric, M3, was determined when a comparison was made between the serif corners. The fourth metric, M4, was determined in operation 354. In operation 354, a determination was made between the difference of the drawn parabola area and the layout serif area.

After the pass/fail report 221 is generated, any necessary modifications in the layout design and/or the mask-making process in accordance with the known pass and fail results are performed. The pass/fail report 221 may be used as a guide to determine what modifications and what changes are necessary in the layout design and the mask-making process. For example, a user may determine whether or not the tooling used to generate the image onto the reticule (i.e., electron beam, laser tool or even the chromium sputtering process), needs to be modified in order to make a compliant test feature. On the other hand, the pass/fail report 221 may also be used to determine whether or not the layout design itself must be changed. For example, it may be determined that the serifs for the layout design in the test feature must be either increased or decreased in size to compensate for any losses that may occur when the digital data of the test feature in the layout design is transferred from the digital data representation onto the reticle.

As may be appreciated, the present invention provides many benefits to a user. The present invention now allows a user to determine the accuracy of a reticle before a photoresist image on a semiconductor wafer is developed. As a result, the costs of determining the accuracy of a reticle is greatly reduced. In the past, users had to develop the photoresist before the accuracy of the reticle could be determined. The present invention avoids this by allowing a user to determine the accuracy of the reticle when the digital data is transferred to the reticle. Therefore, time is saved in that a user does not have to place the reticle into a stepper and wait for the photoresist to develop after the stepping operation is complete. In addition, costs are reduced since a stepper machine and semiconductor wafers do not need to be used.

Although specific examples were provided with regard to the use of chromium on a reticle, it will be understood that other materials can be used and other methods may be used for transferring images onto reticles. For instance, other materials may be used for phase shifted reticles and may be deposited on the reticle. In addition, the glass itself can be masked and etched. Furthermore, other types of reticle materials can also be used instead of glass, such as, reflective reticles, non-glass substrates, and reticles used in Vacuum Ultra Violet (VUV) systems.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A method for inspecting features on a reticle, comprising:

providing a layout design of a test feature;

transferring the layout design of the test feature onto the reticle;

capturing an image of the transferred layout design; and comparing the captured image of the transferred layout design against the layout design of the test feature to ascertain deviations between -the captured image and the layout design;

wherein the ascertaining deviations between the captured image and the layout design includes determining a diagonal difference.

2. A method for inspecting features on a reticle as recited in claim 1, further comprising:

performing a preliminary metric between the test feature of the layout design and the transferred layout design to determine whether the transferred layout design is acceptable.

3. A method for inspecting features on a reticle as recited in claim 1, wherein the layout design of the test feature is digital data.

4. A method for inspecting features on a reticle as recited in claim 1, wherein the operation of transferring the layout design of the test feature onto the reticle is done using one of a laser tool and an electron beam writing tool.

5. A method for inspecting features on a reticle as recited in claim 1, wherein the operation of transferring the layout design of the test feature onto the reticle includes:

depositing a layer onto the reticle; and etching portions of the layer.

6. A method for inspecting features on a reticle as recited in claim 1, wherein the image of the transferred layout design is captured using a scanning electron microscope (SEM).

7. A method for inspecting features on a reticle as recited in claim 1, wherein the image of the transferred layout design is a rectangle that includes at least a first side and a second side.

8. A method for inspecting features on a reticle as recited in claim 7, further comprising:

resizing the rectangle and the image of the transferred layout design such that the at least first side of the rectangle is equal in length to the at least second side of the rectangle to form a resized image of the transferred layout design.

9. A method for inspecting features on a reticle as recited in claim 8, further comprising:

comparing the resized image of the transferred layout design with the layout design of the test feature; and resizing the resized image of the transferred layout design such that the image of the transferred layout design is equal in size to the layout design of the test feature, the resizing of the resized image defining a second resized image.

10. A method for inspecting features on a reticle as recited in claim 9, further comprising:

overlaying the layout design of the test feature onto the second resized image of the transferred layout design; and comparing at least one corner of the second resized image of the transferred layout design with at least one serif of the layout design of the test feature.

11. A method for inspecting features on a reticle as recited in claim 10, further comprising:

ascertaining whether the at least one corner of the image of the transferred layout design passes or fails a metric.

12. A method of ascertaining a degree of distortion of features of a reticle, comprising:

providing a test feature;

transferring the test feature to a reticle to create a transferred test feature;

comparing the transferred test feature with the test feature to ascertain the degree of distortion and whether modifications of the test feature are necessary to compensate for the degree of distortion of the transferred test feature;

wherein ascertaining the degree of distortion includes determining a diagonal difference.

13. A method of ascertaining a degree of distortion of features of a reticle as recited in claim 12, wherein the test feature is digital data.

14. A method of ascertaining a degree of distortion of features of a reticle as recited in claim 12, wherein the test feature of the layout design is transferred to the reticle using one of a laser tool and an electron beam writing tool.

15. A method of ascertaining a degree of distortion of features of a reticle as recited in claim 12, wherein the operation of transferring the test feature to the reticle includes:

depositing a layer onto the reticle; and etching portions of the layer.

16. A method of ascertaining a degree of distortion of features of a reticle as recited in claim 12, further including:

creating an image of the transferred test feature by obtaining a scanning electron microscope image of the transferred test feature after the transferred test feature is transferred to a reticle.

17. A method of ascertaining a degree of distortion of features of a reticle as recited in claim 16, further comprising:

performing a preliminary metric between the test feature and th e image of the transferred test feature to determine whether the transferred test feature is acceptable.

18. A method of ascertaining a degree of distortion of features of a reticle as recited in claim 16, wherein the image of the transferred test feature further includes a rectangle having at least a first side and at least a second side.

19. A method of ascertaining a degree of distortion of features of a reticle as recited in claim 18, further comprising:

resizing the rectangle of the transferred test feature such that the at least first side of the rectangle is equal in length to the at least second side of the rectangle to form a resized image of the transferred test feature.

20. A method of ascertaining a degree of distortion of features of a reticle as recited in claim 19, further comprising:

comparing the resized image of the transferred test feature with the test feature; and resizing the resized image of the transferred test feature such that the resized image of the transferred test feature is equal in size to the test feature, the resizing of the resized image of the transferred test feature defining a second resized image.

21. A method of ascertaining a degree of distortion of features of a reticle as recited in claim 20, further comprising:

overlaying the test feature onto the second resized image; and comparing at least one corner of the second resized image with at least one serif of the test feature.

22. A method of ascertaining a degree of distortion of features of a reticle as recited in claim 21, further comprising:

ascertaining whether the at least one corner of the second resized image passes or fails a metric.

23. A computer readable media having program instruction for carrying out a method of ascertaining a degree of distortion of features of a reticle, comprising:

programming instructions for providing test features;

programming instructions for capturing a transferred test feature that is a result of a transfer of the test feature to a reticle; and programming instructions for comparing the transferred test feature with the test feature to ascertain the degree of distortion and whether modifications of the test feature are necessary to compensate for the degree of distortion of the transferred test feature;

wherein ascertaining the degree of distortion includes determining a diagonal difference.

24. A computer readable media having program instructions for carrying out a method of ascertaining a degree of distortion of features of a reticle as recited in claim 23, wherein the test feature is digital data.

25. A computer readable media having program instructions for carrying out a method of ascertaining a degree of distortion of features of a reticle as recited in claim 23, further comprising:

programming instructions for creating an image of the transferred test feature by obtaining a scanning electron microscope image of the transferred test feature after the transferred test feature is transferred to a reticle.

26. A computer readable media having program instructions for carrying out a method of ascertaining a degree of distortion of features of a reticle as recited in claim 25, further comprising:

programming instructions for performing a preliminary metric between the image of the test feature and the transferred test feature to determine whether the transferred test feature is acceptable.

27. A computer readable media having program instructions for carrying out a method of ascertaining a degree of distortion of features of a reticle as recited in claim 25, wherein the image of the transferred test feature further includes a rectangle having at least a first side and at least a second side.

28. A computer readable media having program instructions for carrying out a method of ascertaining a degree of distortion of features of a reticle as recited in claim 27, further comprising:

programming instructions for resizing the rectangle such that the at least first side of the rectangle is equal in length to the at least second side of the rectangle to form a resized image of the transferred test feature.

29. A computer readable media having program instructions for carrying out a method of ascertaining a degree of distortion of features of a reticle as recited in claim 28, further comprising:

programming instructions for comparing the resized image of the transferred test feature with the test feature; and programming instructions for resizing the resized image of the transferred test feature such that resized image of the transferred test feature is equal in size to the test feature, the resizing of the resized image of the transferred test feature defining a second resized image.

30. A computer readable media having program instructions for carrying out a method of ascertaining a degree of distortion of features of a reticle as recited in claim 29, further comprising:

programming instructions for overlaying the test feature of the layout design onto the second resized image; and programming instructions for comparing at least one corner of the second resized image with at least one serif of the test feature.

31. A computer readable media having program instructions for carrying out a method for ascertaining a degree of distortion of features of a reticle as recited in claim 30, further comprising:

programming instructions for ascertaining whether t he at least one corner of the second resized image passes or fails a metric.

* * * * *